United States Patent
Rich et al.

(10) Patent No.: US 11,944,369 B2
(45) Date of Patent: Apr. 2, 2024

(54) FORCEPS WITH LINEAR TRIGGER KICKOUT MECHANISM

(71) Applicant: Covidien LP, Mansfield, MA (US)

(72) Inventors: Jennifer L. Rich, Parker, CO (US); Craig V. Krastins, Arvada, CO (US); Daniel W. Mercier, Erie, CO (US); Kelley D. Goodman, Erie, CO (US); Grant T. Sims, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/129,262

(22) Filed: Mar. 31, 2023

(65) Prior Publication Data

US 2023/0248418 A1     Aug. 10, 2023

Related U.S. Application Data

(62) Division of application No. 16/994,278, filed on Aug. 14, 2020, now Pat. No. 11,628,008.

(Continued)

(51) Int. Cl.
    *A61B 18/14*     (2006.01)
    *A61B 18/12*     (2006.01)
    (Continued)

(52) U.S. Cl.
    CPC ...... *A61B 18/1442* (2013.01); *A61B 18/1206* (2013.01); *A61B 2017/00367* (2013.01);
    (Continued)

(58) Field of Classification Search
    CPC ........ A61B 2090/0801; A61B 18/1442; A61B 18/1206; A61B 2018/00202; A61B 2018/0063; A61B 2018/1455

See application file for complete search history.

(56) References Cited

U.S. PATENT DOCUMENTS

D249,549 S     9/1978    Pike
D263,020 S     2/1982    Rau, III
              (Continued)

FOREIGN PATENT DOCUMENTS

CN     201299462 Y    9/2009
CN     202086577 U    12/2011
              (Continued)

OTHER PUBLICATIONS

Reducing Needlestick Injuries in the Operating Room Sales/Product Literature 2001_ (1 page).

(Continued)

*Primary Examiner* — Sean W Collins
(74) *Attorney, Agent, or Firm* — Carter, DeLuca & Farrell LLP

(57) ABSTRACT

A forceps includes shaft members each having a jaw member disposed at a distal end thereof and configured move the jaw members between open and closed position. A knife deployment mechanism includes a trigger moveable along a longitudinal axis to deploy a knife between retracted and extended positions between the jaw members, the knife deployment mechanism including links that cooperate to actuate the knife. A knife kickout mechanism is pivotably coupled to one link and is configured to engage a ramp disposed in a shaft member upon approximation of the shaft members, the knife kickout is configured to cooperate with the links to urge the knife back to an at rest position upon the opening of the shaft members.

9 Claims, 30 Drawing Sheets

Related U.S. Application Data

(60) Provisional application No. 62/990,277, filed on Mar. 16, 2020.

(51) Int. Cl.
  *A61B 17/00*   (2006.01)
  *A61B 17/072*   (2006.01)
  *A61B 17/285*   (2006.01)
  *A61B 18/00*   (2006.01)
  *A61B 90/00*   (2016.01)

(52) U.S. Cl.
  CPC .......... *A61B 17/072* (2013.01); *A61B 17/285* (2013.01); *A61B 2018/00202* (2013.01); *A61B 2018/00589* (2013.01); *A61B 2018/00595* (2013.01); *A61B 2018/0063* (2013.01); *A61B 2018/00708* (2013.01); *A61B 2018/00916* (2013.01); *A61B 2018/1455* (2013.01); *A61B 2018/1457* (2013.01); *A61B 2018/1475* (2013.01); *A61B 2090/0801* (2016.02)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| 4,763,669 A | 8/1988 | Jaeger |
| D298,353 S | 11/1988 | Manno |
| D299,413 S | 1/1989 | DeCarolis |
| 5,100,420 A | 3/1992 | Green et al. |
| 5,258,001 A | 11/1993 | Corman |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| 5,344,424 A | 9/1994 | Roberts et al. |
| D354,564 S | 1/1995 | Medema |
| D358,887 S | 5/1995 | Feinberg |
| 5,540,685 A | 7/1996 | Parins et al. |
| 5,578,052 A | 11/1996 | Koros et al. |
| 5,611,808 A | 3/1997 | Hossain et al. |
| 5,618,294 A | 4/1997 | Aust et al. |
| D384,413 S | 9/1997 | Zlock et al. |
| 5,665,100 A | 9/1997 | Yoon |
| 5,752,644 A | 5/1998 | Bolanos et al. |
| H1745 H | 8/1998 | Paraschac |
| 5,814,043 A | 9/1998 | Shapeton |
| D402,028 S | 12/1998 | Grimm et al. |
| D408,018 S | 4/1999 | McNaughton |
| 5,913,874 A | 6/1999 | Berns et al. |
| 5,960,544 A | 10/1999 | Beyers |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| H1904 H | 10/2000 | Yates et al. |
| 6,293,954 B1 | 9/2001 | Fogarty et al. |
| D449,886 S | 10/2001 | Tetzlaff et al. |
| 6,329,778 B1 | 12/2001 | Culp et al. |
| 6,334,861 B1 | 1/2002 | Chandler et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossain et al. |
| H2037 H | 7/2002 | Yates et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,673,092 B1 | 1/2004 | Bacher |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,641,653 B2 | 1/2010 | Dalla Betta et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,854,185 B2 | 12/2010 | Zhang et al. |
| D630,324 S | 1/2011 | Reschke |
| 7,896,878 B2 | 3/2011 | Johnson et al. |
| D649,249 S | 11/2011 | Guerra |
| D649,643 S | 11/2011 | Allen, IV et al. |
| 8,147,489 B2 | 4/2012 | Moses et al. |
| D661,394 S | 6/2012 | Romero et al. |
| 8,298,233 B2 | 10/2012 | Mueller |
| D670,808 S | 11/2012 | Moua et al. |
| 8,366,709 B2 | 2/2013 | Schechter et al. |
| 8,394,096 B2 | 3/2013 | Moses et al. |
| D680,220 S | 4/2013 | Rachlin |
| 8,409,246 B2 | 4/2013 | Kerr et al. |
| 8,409,247 B2 | 4/2013 | Garrison et al. |
| 8,425,504 B2 | 4/2013 | Orton et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,591,510 B2 | 11/2013 | Allen, IV et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,734,445 B2 | 5/2014 | Johnson et al. |

(56) References Cited

U.S. PATENT DOCUMENTS

| | | |
|---|---|---|
| 8,740,898 B2 | 6/2014 | Chojin et al. |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,858,553 B2 | 10/2014 | Chojin |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,888,775 B2 | 11/2014 | Nau, Jr. et al. |
| 8,898,888 B2 | 12/2014 | Brandt et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,211,657 B2 | 12/2015 | Ackley et al. |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 10,653,475 B2 | 5/2020 | Gutti |
| 11,628,008 B2 | 4/2023 | Rich et al. |
| 2003/0018332 A1 | 1/2003 | Schmaltz et al. |
| 2003/0109875 A1 | 6/2003 | Tetzlaff et al. |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0179499 A1 | 8/2007 | Garrison |
| 2007/0260241 A1 | 11/2007 | Dalla Betta et al. |
| 2008/0215048 A1 | 9/2008 | Hafner et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179545 A1 | 7/2010 | Twomey et al. |
| 2010/0179547 A1 | 7/2010 | Cunningham et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0054469 A1 | 3/2011 | Kappus et al. |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1* | 4/2012 | Artale .................. A61B 17/285 606/207 |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184988 A1 | 7/2012 | Twomey et al. |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |

(56) References Cited

U.S. PATENT DOCUMENTS

| | | |
|---|---|---|
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke et al. |
| 2013/0178852 A1 | 7/2013 | Allen, IV et al. |
| 2013/0185922 A1 | 7/2013 | Twomey et al. |
| 2013/0190753 A1 | 7/2013 | Garrison |
| 2013/0190760 A1 | 7/2013 | Allen, IV |
| 2013/0197503 A1 | 8/2013 | Orszulak |
| 2013/0226177 A1 | 8/2013 | Brandt |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2016/0157925 A1 | 6/2016 | Artale et al. |
| 2016/0175031 A1 | 6/2016 | Boudreaux |
| 2017/0128120 A1 | 5/2017 | Cho et al. |
| 2018/0325580 A1* | 11/2018 | Sims .............. A61B 18/1233 |
| 2018/0353235 A1* | 12/2018 | Gutti .............. A61B 18/1442 |

FOREIGN PATENT DOCUMENTS

| | | |
|---|---|---|
| CN | 102525639 A | 7/2012 |
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 3627221 A1 | 2/1988 |
| DE | 8712328 U1 | 2/1988 |
| DE | 0430388202 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1159926 A2 | 12/2001 |
| EP | 1281878 A1 | 2/2003 |
| EP | 1532932 A1 | 5/2005 |
| EP | 2301468 A1 | 3/2011 |
| EP | 2353535 A1 | 8/2011 |
| EP | 2436327 A1 | 4/2012 |
| EP | 2436330 A1 | 4/2012 |
| EP | 2529681 A1 | 12/2012 |
| EP | 3072467 A1 | 9/2016 |
| JP | 61501068 | 9/1984 |
| JP | H1024051 | 1/1989 |
| JP | 6502328 | 3/1992 |
| JP | 55106 | 1/1993 |
| JP | H0540112 A | 2/1993 |
| JP | 6121797 | 5/1994 |
| JP | 6285078 | 10/1994 |
| JP | H06343644 A | 12/1994 |
| JP | H07265328 A | 10/1995 |
| JP | H0856955 A | 3/1996 |
| JP | 08252263 | 10/1996 |
| JP | H08289895 | 11/1996 |
| JP | H08317934 | 12/1996 |
| JP | H08317936 | 12/1996 |
| JP | 09000538 | 1/1997 |
| JP | H0910223 A | 1/1997 |
| JP | 9122138 | 5/1997 |
| JP | 0010000195 | 1/1998 |
| JP | H10155798 A | 6/1998 |
| JP | 1147149 | 2/1999 |
| JP | H1147150 A | 2/1999 |
| JP | H11169381 | 6/1999 |
| JP | H11192238 | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2001003400 | 11/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 6511401 | 5/2019 |
| SU | 401367 A1 | 10/1973 |
| WO | 9400059 | 1/1994 |
| WO | 9923933 | 5/1999 |
| WO | 0024330 | 5/2000 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 02080786 | 10/2002 |
| WO | 02080793 A1 | 10/2002 |
| WO | 2006021269 A1 | 3/2006 |

(56) References Cited

FOREIGN PATENT DOCUMENTS

| WO | 2005110264 A3 | 4/2006 |
|---|---|---|
| WO | 2008040483 A1 | 4/2008 |
| WO | 2011018154 A1 | 2/2011 |
| WO | 2013009758 A2 | 1/2013 |
| WO | 2013022928 A1 | 2/2013 |
| WO | 2013134044 A1 | 9/2013 |
| WO | 2015017991 A1 | 2/2015 |

OTHER PUBLICATIONS

Levy et al., "Update on Hysterectomy—New Technologies and Techniques" OBG Management, Feb. 2003. (15 pages.).
Barbara Levy, "Use of a New Vessel Ligation Device During Vaginal Hysterectomy" FIGO 2000, Washington, D.C .. (1 Page).
Vallfors et al., Automatically Controlled Bipolar Electrocoagulation— "COA-COMP", Neurosurg. Rev. (1984), pp. 187-190.
Examination Report No. 1 issued in corresponding Australian Application No. 2018201752 dated Aug. 8, 2018, 10 pages.
Extended European Search Report issued in corresponding application No. 18171773.7 dated Oct. 8, 2018, 7 pages.
Canadian Office Action issued in Canadian Application No. 2,997,771 dated Jan. 4, 2019, 3 pages.
U.S. Appl. No. 08/926,869, filed Sep. 10, 1997, James G. Chandler, abandoned.
U.S. Appl. No. 09/177,950, filed Oct. 23, 1998, Randel A. Frazier.
U.S. Appl. No. 09/387,883, filed Sep. 1, 1999, Dale F. Schmaltz, abandoned.
U.S. Appl. No. 09/591,328, filed Jun. 9, 2000 Thomas P. Ryan, abandoned.
U.S. Appl. No. 12/336,970, filed Dec. 17, 2008, Paul R. Sremeich, abandoned.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al., "Comparison of Healing Process Following Ligation with Sutures and Bipolar Vessel Sealing" Surgical Technology International (2001).
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.
IgaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" . Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, op. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery {2001) 71 .9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
E. David Crawford, "Use of a Novel Vessel Sealing Technology in Management of the Dorsal Veinous Complex" Sales! Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue" MICCAI 2005; LNCS 3750 pp. 624-632 Dated: 2005.
McLellan et al. "Vessel Sealing for Hemostasis During Pelvic Surgery" Int3 1 Federation of Gynecology and Obstetrics FIGO World Congress 2000, Washington, D.C.
McLellan et al. "Vessel Sealing for Hemostasis During Gynecologic Surgery" Sales/Product Literature 1999.

(56) References Cited

OTHER PUBLICATIONS

"Electrosurgery: A Historical Overview" Innovations in Electrosurgery; Sales/Product Literature; Dec. 31, 2000, 6 pages.

Johnson et al. "Evaluation of a Bipolar Electrothermal Vessel Sealing Device in Hemorrhoidectomy" Sales/Product Literature; Jan. 2004, 1 page.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Heniford et al. "Initial Results with an Electrothermal Bipolar Vessel Sealer" Surgical Endoscopy (2000) 15:799-801. (4 pages).

\* cited by examiner

FORCEPS WITH LINEAR TRIGGER KICKOUT MECHANISM

CROSS REFERENCE TO RELATED APPLICATION

This application claims the benefit of and priority to U.S. application Ser. No. 16/994,278 filed Aug. 14, 2020 which claims priority to U.S. Provisional Application Ser. No. 62/990,277 filed Mar. 16, 2020, the entire contents of both of which being incorporated by reference herein.

BACKGROUND

Technical Field

The present disclosure relates to electrosurgical instruments and, more particularly, to electrosurgical forceps for grasping, treating, and/or dividing tissue.

Background of Related Art

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical forceps have been designed which incorporate a knife configured to effectively sever tissue after treating the tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

Provided in accordance with the present disclosure is an electrosurgical forceps including first and second shaft members each having a jaw member disposed at a distal end thereof, the first and second shaft members configured to rotate about a first pivot to move the jaw members between an open position and a closed position. The first and second shaft members define a longitudinal axis therebetween. A knife deployment mechanism is disposed within the first shaft member and includes a trigger moveable along the longitudinal axis to deploy a knife operably coupled thereto between a retracted position relative to the jaw members and an extended position between the jaw members. The knife deployment mechanism includes a first link and a second link that cooperate with a knife carrier to actuate the knife from an at rest position to an extended position between the jaw members upon actuation of the trigger. A trigger carrier includes a channel defined therein configured to support the trigger upon actuation thereof. A trigger pin operably couples to the trigger and is slidable within the trigger channel upon actuation of the trigger. A knife kickout mechanism pivotably couples to the second link and is configured to engage a ramp disposed in the second shaft member upon approximation of the first and second shaft members. The knife kickout is configured to cooperate with the first and second links to urge the knife back to the retracted position upon the opening of the first and second shaft members.

In aspects according to the present disclosure, the trigger pin is configured to engage the knife kickout mechanism to urge the knife kickout mechanism into engagement with the ramp. In other aspects according to the present disclosure, the knife kickout mechanism is configured to engage the trigger pin upon opening of the first and second shaft members to urge the trigger pin and the trigger back to an at rest position.

In aspects according to the present disclosure, one or both of the first and second links is operably coupled to a spring to bias the knife in the retracted position. In other aspects according to the present disclosure, the first link is configured to travel in an arcuate channel defined within the first shaft member to facilitate smooth translation of the knife.

In aspects according to the present disclosure, the knife kickout mechanism is configured to rotate about a second pivot operably coupled to the second link. In other aspects according to the present disclosure, the path of rotation of the knife kickout mechanism about the second pivot is different than the path of the rotation of the first and second shaft members about the first pivot. In still other aspects according to the present disclosure, the knife kickout mechanism includes an upper portion having a curved surface to facilitate engagement and disengagement with the ramp.

In other aspects according to the present disclosure, the second link cooperates with a third link operably coupled to the trigger to actuate the knife. In other aspects according to the present disclosure, the knife kickout mechanism is disposed on opposite sides of the second link and the third link. In yet other aspects according to the present disclosure, the third link is configured to operably engage the knife kickout mechanism to facilitate return of the knife kickout mechanism to an at rest position.

Provided in accordance with the present disclosure is an electrosurgical forceps including first and second shaft members each having a jaw member disposed at a distal end thereof, the first and second shaft members configured to rotate about a first pivot to move the jaw members between an open position and a closed position. The first and second shaft members define a longitudinal axis therebetween. A knife deployment mechanism is disposed within the first shaft member and includes a trigger moveable along the longitudinal axis to deploy a knife operably coupled thereto between a retracted position relative to the jaw members and an extended position between the jaw members. The knife deployment mechanism includes a first link, a second link and a third link that cooperate with a knife carrier to actuate the knife from the retracted position to the extended position between the jaw members upon actuation of the trigger. A knife kickout mechanism is pivotably coupled to the second link and is configured to engage a ramp disposed in the second shaft member upon approximation of the first and second shaft members. The knife kickout mechanism is configured to cooperate with the first, second and third links to urge the knife back to the retracted position upon the opening of the first and second shaft members.

In aspects according to the present disclosure, the third link is configured to operably engage the knife kickout mechanism to facilitate return of the knife kickout mechanism to an at rest position. In other aspects according to the present disclosure, one of the first and second links is operably coupled to a spring to bias the knife in the retracted position.

In aspects according to the present disclosure, the first link is configured to travel in an arcuate channel defined within the first shaft member to facilitate smooth translation of the knife. In other aspects according to the present disclosure, the knife kickout mechanism is configured to rotate about a second pivot operably coupled to the second link. In yet other aspects according to the present disclosure, the path of rotation of the knife kickout mechanism about the second pivot is different than the path of the rotation of the first and second shaft members about the first pivot.

In aspects according to the present disclosure, the knife kickout mechanism includes an upper portion having a curved surface to facilitate engagement and disengagement with the ramp. In other aspects according to the present disclosure, the knife kickout mechanism is disposed on opposite sides of the second link and the third link.

In aspects according to the present disclosure, the third link is configured to operably engage the knife kickout mechanism if the knife is inhibited from returning to the retracted position, the range of motion of the third link upon returning to an at rest position configured to operably engage the knife kickout mechanism and facilitate the return of the knife kickout mechanism and the trigger to an at rest position.

BRIEF DESCRIPTION OF THE DRAWINGS

Various aspects and features of the present electrosurgical forceps are described hereinbelow with reference to the drawings wherein like numerals designate identical or corresponding elements in each of the several views.

DETAILED DESCRIPTION

Figure 1A:
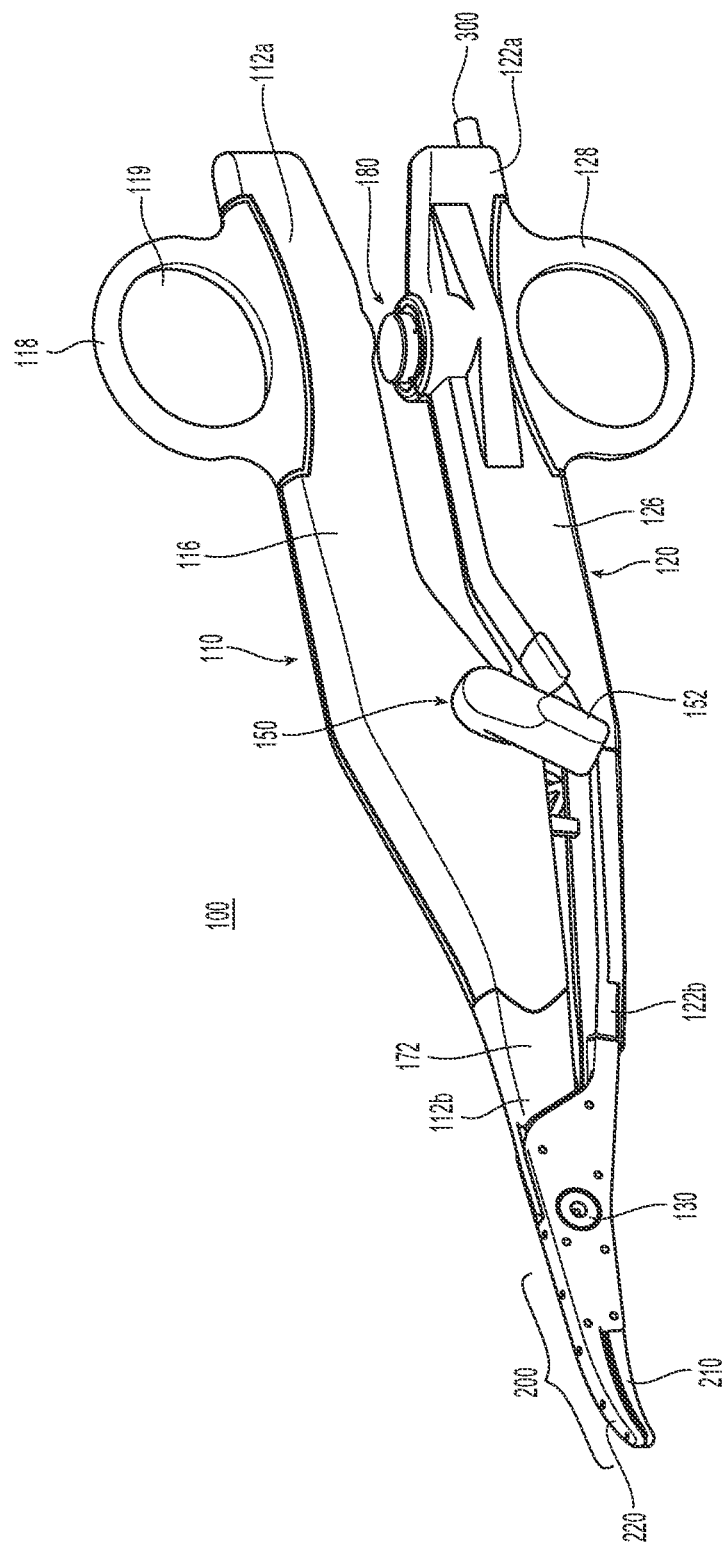
FIG. 1A-1F are various views of a prior art electrosurgical forceps including a knife lockout mechanism.
Figure 1B:
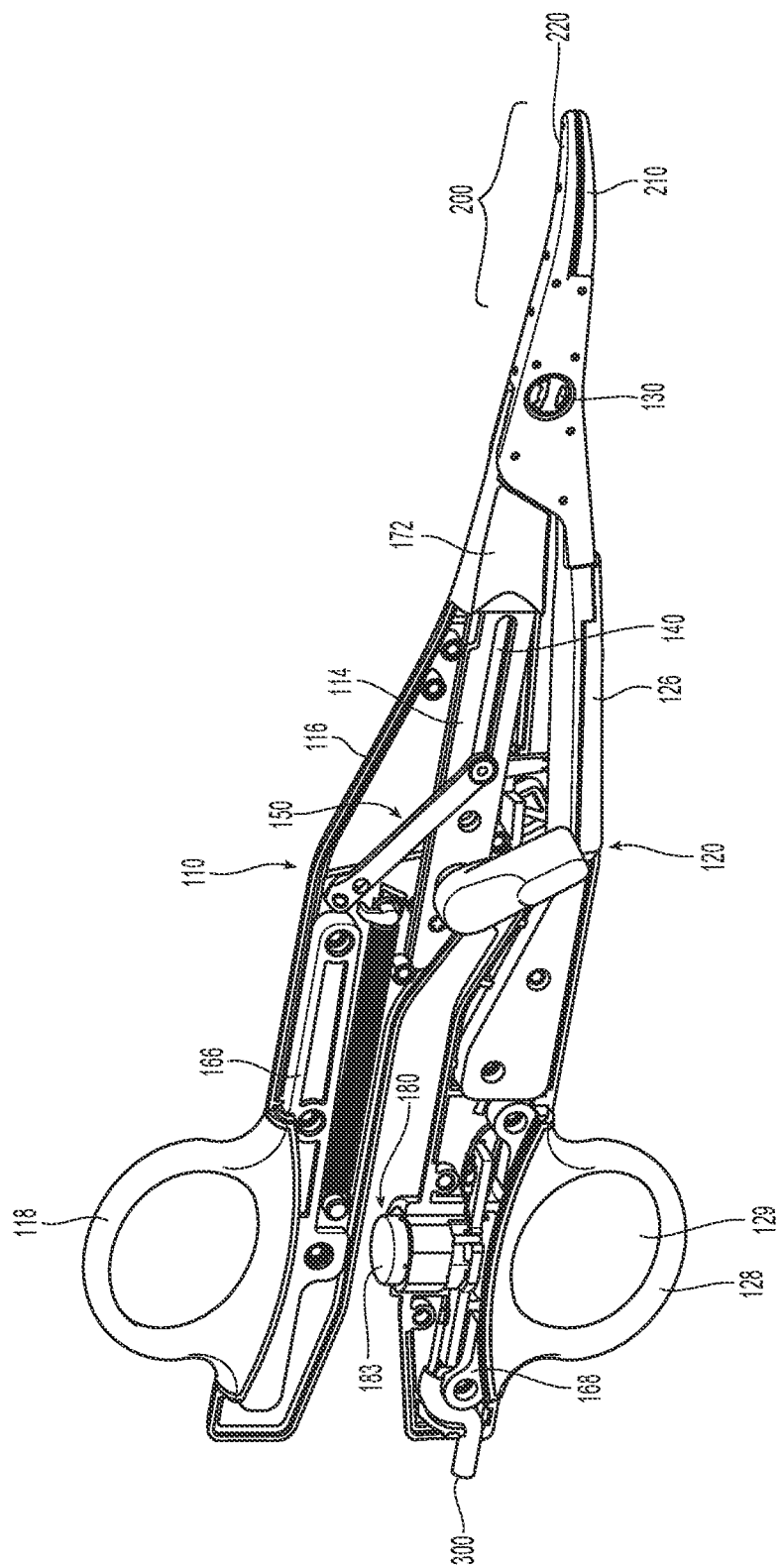

The present disclosure describes electrosurgical forceps for grasping, treating, and/or dividing tissue. The forceps includes two shafts each having a jaw member disposed at a distal end thereof and movable between open and closed positions to grasp tissue. The electrosurgical forceps also includes a knife configured to divide grasped tissue following treatment of the tissue (e.g., a tissue seal cycle). A knife lockout works in conjunction with the shafts to prevent deployment of the knife prior to the shafts reaching a sufficiently-approximated position corresponding to a sufficiently-closed position of jaw members as well as to prevent deployment of the knife during treatment of tissue.

Referring generally to FIGS. 1A-1F, a forceps 100 provided in accordance with the present disclosure includes first and second shafts 110, 120 each having a proximal end portion 112a, 122a and a distal end portion 112b, 122b. An end effector assembly 200 of forceps 100 includes first and second jaw members 210, 220 extending from distal end portions 112b, 122b of shafts 110, 120, respectively. Forceps 100 further includes a pivot member 130 pivotably coupling first and second shafts 110, 120 with one another, a knife 140 (FIG. 1B), a knife deployment mechanism 150 for selectively deploying knife 140 relative to end effector assembly 200, a knife lockout 170 (FIGS. 1D-1F) for preventing deployment of knife 140 prior to sufficient closure of jaw members 210, 220, and a switch assembly 180 including a depressible activation button 183 for enabling the selective supply of electrosurgical energy to end effector assembly 200. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

The internal working components of the prior art forceps of FIGS. 1A-1F and, in particular, the inner-working components of the knife lockout 170 are disclosed in commonly-owned U.S. patent application Ser. No. 15/617,283, the entire contents of which being incorporated by reference herein.

Continuing with reference to FIGS. 1A-1F, knife deployment mechanism 150 is coupled to shaft 110 and generally includes a pair of opposed triggers 152 (FIG. 1D) extending from either side of shaft 110, a first linkage 154, a second linkage 156, and a biasing spring 158. Knife deployment mechanism 150 is disposed within outer housing 116 of shaft 110 with the exception of opposed triggers 152 which extend from either side of outer housing 116. First linkage 154 is configured for positioning on one side of inner frame 114 (FIG. 1C) of shaft 110 and includes a pair of integral (or otherwise engaged) pivot bosses (not shown) extending from either side thereof at a first end portion of first linkage 154. Each pivot boss enables engagement of opposed triggers 152 therewith on either side of shaft 110, e.g., via press-fitting, adhesion, or other suitable engagement.

Figure 1C:
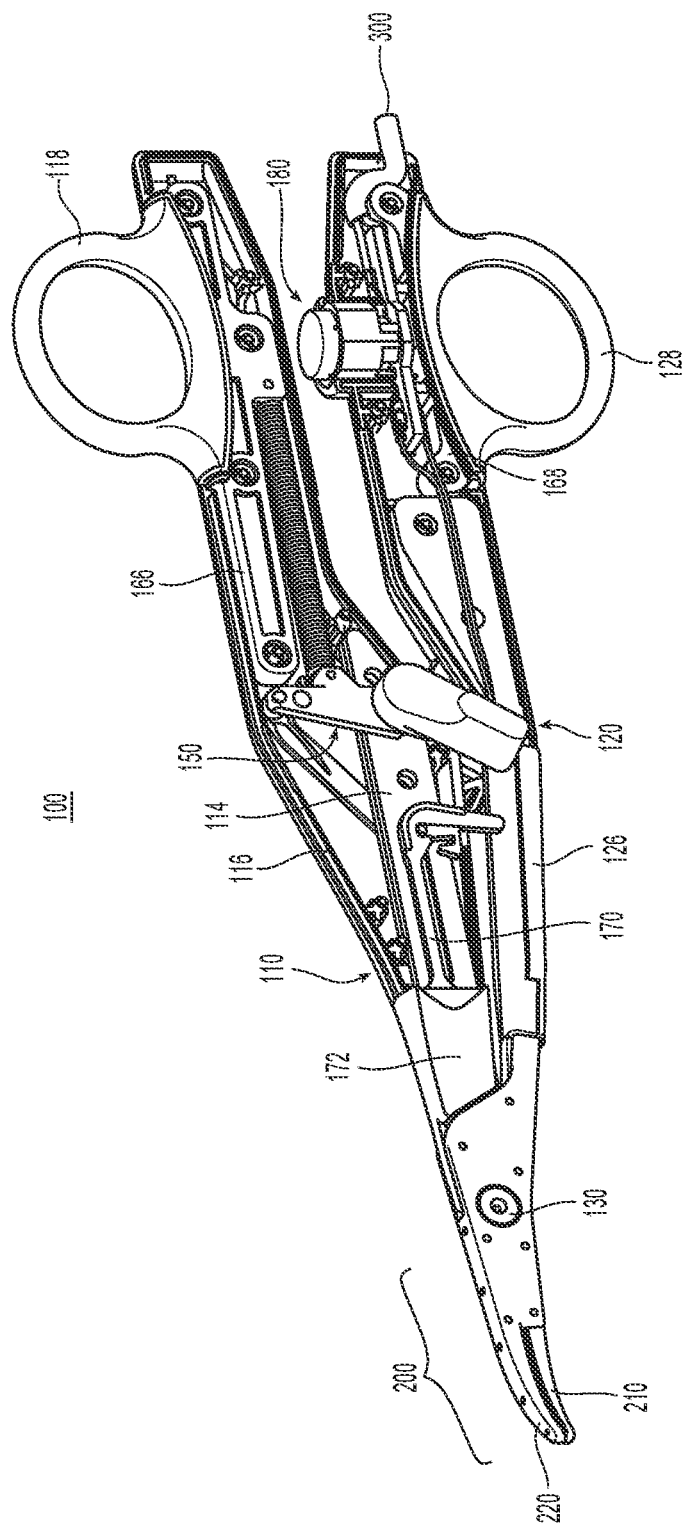

A proximal end portion of second linkage 156 is pivotably coupled to first linkage 154 at a second end portion of first linkage 154. A distal end portion of second linkage 156 is pivotably coupled to knife 140 via a pivot pin 163 (FIG. 1F). Pivot pin 163 may be integrally formed with second linkage 156, e.g., as a post extending therefrom, or may be a separate component from second linkage 156. Pivot pin 163 extends transversely through a longitudinal slot 115e (FIG. 1E) of inner frame 114 of shaft 110 such that pivot pin 163 is constrained to longitudinal movement within longitudinal slot 115e. Second linkage 156 is disposed on one side of inner frame 114, which may be the same side as first linkage 154 or the opposite side (as shown). In either configuration, pivot pin 163 extends from second linkage 156 and through longitudinal slot 115e such that a portion of pivot pin 163 protrudes laterally from the opposite side of inner frame 114.

Biasing spring 158 may be configured as an extension spring or other suitable biasing spring 158. A distal end portion of biasing spring 158 is engaged to first linkage 154 and a proximal end portion of biasing spring 158 is engaged to a support plate 166 (FIG. 1C). Spring 158 may be engaged to any moveable components of the knife deployment mechanism 150. Support plate 166 includes handle 118 of shaft 110 integrally formed therewith or otherwise engaged thereto, and may be secured within outer housing 116 in any suitable fashion, e.g., via protrusion-aperture engagement. Support plate 166 provides increased structural support to shaft 110 to inhibit splaying of shafts 110, 120 during use. Shaft 120 similarly includes a support plate 168 integrally formed with or otherwise engaging handle 128 of shaft 120 and secured to outer housing 126, although support plate 168 need not extend distally as with support plate 166.

Biasing spring 158 biases first linkage 154 towards a first orientation, corresponding to the un-actuated position of triggers 152 and the proximal-most position of second linkage 156, thereby biasing knife 140 towards a retracted position (e.g., a proximal-most position of knife 140). Upon rotation of either of triggers 152 relative to shaft 110, first linkage 154 is rotated against the bias of biasing spring 158 to thereby urge second linkage 156 distally such that pivot pin 163 is driven distally through longitudinal slot 115e (FIG. 1E) to urge knife 140 from the retracted position towards an extended position, wherein knife 140 extends through a slot defined in pivot member 130, a channel of body plate 115, and knife channels of jaw members 210, 220.

In use, a distal portion of knife 140 is configured to reciprocate through the slot of pivot member 130 to translate through knife channels of jaw members 210, 220 in response to actuation of either trigger 152. Knife deployment mechanism 150 is operably positioned on shaft 110 and relative to shaft 120 such that triggers 152 only slightly extend beyond the height dimension of forceps 100 in the vicinity of triggers 152, in the furthest-approximated position of shafts 110, 120. As a result of this configuration, forceps 100 benefits from a low-profile design that reduces the chances of triggers 152 catching on the surgeon, patient, or on nearby objections during use and/or as forceps 100 is inserted and withdrawn from the surgical site.

Figures 1D, 1E:
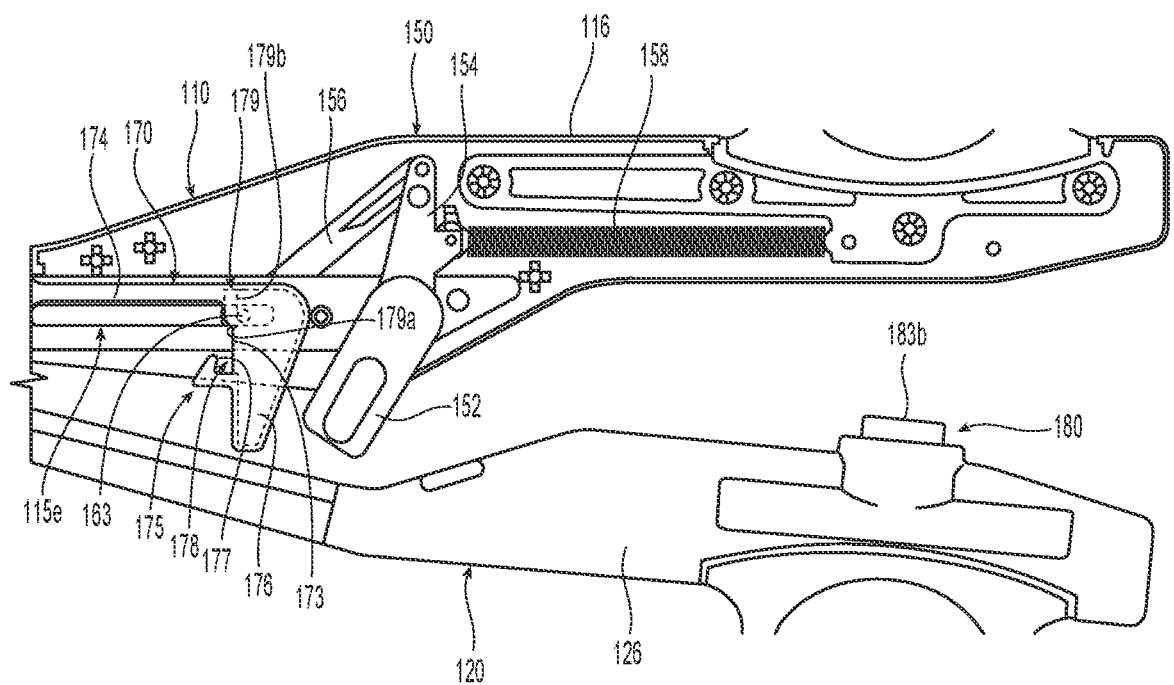
Figure 1F:
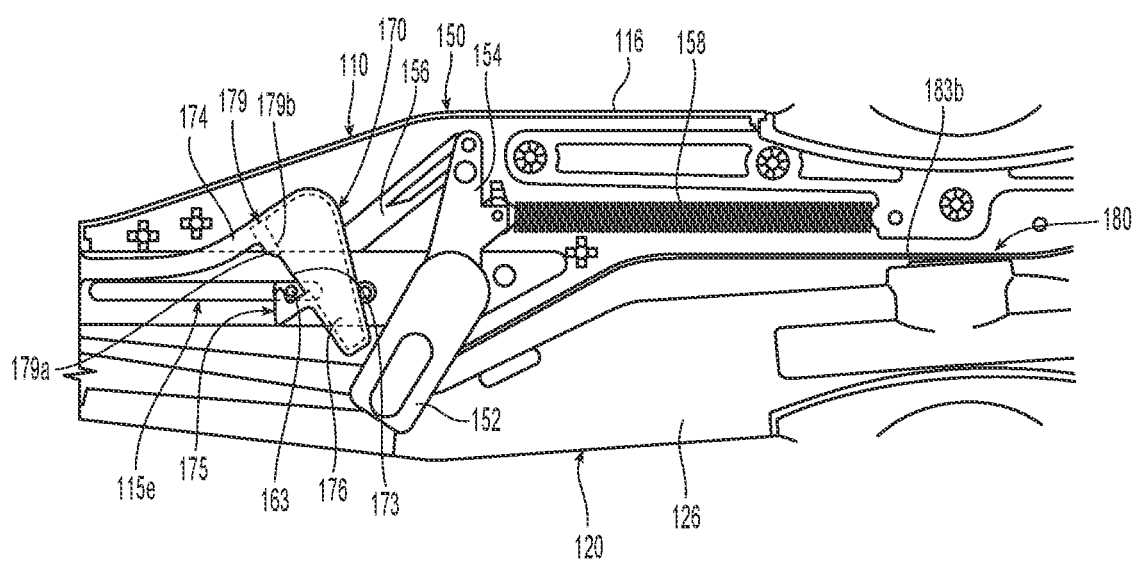

Turning to FIGS. 1D-1F, knife lockout 170 works in conjunction with shafts 110, 120 to prevent deployment of knife 140 prior to shafts 110, 120 reaching a sufficiently-approximated position corresponding to a sufficiently-closed position of jaw members 210, 220. Knife lockout 170 includes a body 172 (FIGS. 1A-1C) that is disposed about a portion of the inner frame 114 of shaft 110 and forms a portion of outer housing 116 of shaft 110. More specifically, as shown in FIG. 1A, body 172 of knife lockout 170 defines a complementarily-shaped abutting surface with the abutting surface of the adjacent other component(s) of housing 116 such that housing 116 defines a substantially continuous outer surface.

Knife lockout 170 further includes a cantilever arm 174 extending proximally from body 172. Cantilever arm 174 and body 172 may be integrally formed, e.g., via injection molding, or may be attached in any other suitable fashion. Cantilever arm 174 extends along inner frame 114 of shaft 110 on an opposite side of inner frame 114 as compared to second linkage 156 of knife deployment mechanism 150. Cantilever arm 174 defines a relatively narrowed configuration to permit flexing of cantilever arm 174. A finger 176 integrally formed with cantilever arm 174 extends generally perpendicularly from a free end of cantilever arm 174 and through an opening defined in outer housing 116 of shaft 110 towards shaft 120. A first stop 179 is defined at the junction of cantilever arm 174 and finger 176. First stop 179 protrudes from cantilever arm 174 and defines an angled distal wall 179a and a vertical proximal wall 179b. The finger 176 includes a second stop 175 extending distally from a vertical distal wall 173 of finger 176. The second stop 175 defines a vertical proximal wall 177 that is generally parallel to vertical distal wall 173 of finger 176. A nook 178 is defined between vertical proximal wall 177 of second stop 175 and vertical distal wall 173 of finger 176.

Referring to FIG. 1D, with shafts 110, 120 sufficiently spaced-apart from one another and jaw members 210, 220 in the open position, finger 176 of knife lockout 170 is spaced-apart from outer housing 126 of shaft 120 such that cantilever arm 174 is disposed in an at-rest position. In its at-rest position, cantilever arm 174 extends along and in a generally parallel orientation relative to longitudinal slot 115e of inner frame 114 of shaft 110. Further, vertical proximal wall 179b of first stop 179 is disposed at the proximal end portion of longitudinal slot 115e and prevents distal advancement of pivot pin through longitudinal slot 115e in the at-rest position of cantilever arm 174 and, accordingly, prevents deployment of knife 140.

Referring to FIG. 1E, in order to disengage knife lockout 170 to permit deployment of knife 140, shafts 110, 120 are sufficiently approximated such that jaw members 210, 220 are moved to the closed position (e.g., to grasp tissue therebetween) and a portion of outer housing 126 of shaft 120 contacts finger 176 of knife lockout 170 to urge finger 176 further into housing 116 of shaft 110. However, as shown in the configuration of FIG. 1E, shaft 110 is sufficiently spaced from shaft 120 such that outer housing 116 of shaft 110 is spaced from or otherwise out of engagement with depressible button 183 of switch assembly 180 such that depressible button 183 is not depressed to activate switch assembly 180 for initiating the supply of energy from the energy source (not shown) to jaw members 210, 220. As finger 176 is urged further into housing 116 of shaft 110, cantilever arm 174 is flexed such that vertical proximal wall 179b of first stop 179 is removed from the distal path of pivot pin 163. Once this has been achieved, knife deployment mechanism 150 may be actuated, as detailed above, to advance pivot pin 163 distally through slot to move knife 140 from the retracted position towards the extended position.

Should shafts 110, 120 be moved apart from one another sufficiently such that shaft 120 no longer urges finger 176 to flex cantilever arm 174, cantilever arm 174 is resiliently returned to its at-rest position. If knife 140 is disposed in the retracted position at this point, vertical proximal wall 179b is returned to block the distal path of pivot pin 163. However, if knife 140 is disposed in the deployed position or a partially-deployed position, the return of cantilever arm 174 to its at-rest position does not block the distal path of pivot pin 163 via vertical proximal wall 179b. Rather, upon subsequent return of knife 140 to the retracted position, pivot pin 163 is moved proximally and into contact with angled distal wall 179a of first stop 179, camming therealong and urging cantilever arm 174 to flex from the at-rest position sufficiently so as to enable pivot pin 163 to return to the proximal end of longitudinal slot 115e.

Once pivot pin 163 reaches this position, cantilever arm 174 is returned to the at-rest position and, as a result, vertical proximal wall 179b is returned to blocking the distal path of pivot pin 163, thereby resetting knife lockout 170 to prevent movement of knife 140 from the retracted position towards the extended position until shafts 110, 120 are once again sufficiently approximated. The biasing force of biasing member 158 is sufficient to move pivot pin 163 proximally to deflect cantilever arm 174 and reset knife lockout 170 as detailed above. As such, resetting of knife lockout 170 occurs automatically (if shafts 110, 120 are sufficiently spaced-apart) upon return of knife 140 to the retracted position.

Referring to FIGS. 1E and 1F to activate switch assembly 180 to initiate the supply of energy from the energy source (not shown) to jaw members 210, 220 for sealing tissue grasped between jaw members 210, 220, shafts 110, 120 are further approximated from the approximated position illustrated in FIG. 1E such that finger 176 is urged further into housing 116 of shaft 110 and depressible button 183b is engaged and depressed by a portion of outer housing 116 of shaft 110 to activate switch assembly 180 (FIG. 1F).

As finger 176 is urged further into housing 116 of shaft 110, cantilever arm 174 is further flexed such that vertical proximal wall 179b of first stop 179 remains removed from the distal path of pivot pin 163 and second stop 175 is urged further into housing 116 of shaft 110 such that the portion of pivot pin 163 that extends from second linkage 156 through longitudinal slot 115e is received within nook 178 of second stop 175. Once pivot pin 163 is received within nook 178, vertical proximal wall 177 of second stop 175 prevents distal advancement of pivot pin 163 through longitudinal slot 115e and, accordingly, prevents movement of knife 140 through jaw members 210, 220 during activation of switch assembly 180. In this manner, premature cutting of tissue during delivery of energy to tissue via jaw members 210, 220 (e.g., prior to completion of a tissue sealing cycle) is prevented.

Once a tissue sealing cycle is complete, switch assembly 180 may be deactivated by returning shafts 110, 120 from an energy delivery position illustrated in FIG. 1F to the approximated position illustrated in FIG. 1E such that jaw members 210, 220 remain in the closed position and depressible button 183b is no longer depressed by outer housing 116 of shaft 110. Upon returning to the approximated position illustrated in FIG. 1E, cantilever arm 174 remains sufficiently flexed such that vertical proximal wall 179b of first stop 179 is removed from the distal path of pivot pin 163.

Accordingly, knife deployment mechanism 150 may be actuated, as detailed above, to advance pivot pin 163 distally through slot 115e to move knife 140 from the retracted position towards the extended position to cut tissue grasped between jaw members 210, 220 (e.g., subsequent to completion of sealing the grasped tissue). Following cutting of the grasped tissue, shafts 110, 120 may be moved apart from one another, as detailed above, to the spaced-apart position illustrated in FIG. 1D such that cantilever arm 174 is resiliently returned to its at-rest position to reset knife lockout 170 to prevent movement of knife 140 from the retracted position towards the extended position.

Details relating to the operation of the switch assembly 180 are disclosed in commonly-owned U.S. patent application Ser. No. 15/617,283, the entire contents of which being incorporated by reference herein.

Cantilever arm 174 in use, functions as follows: when the shaft members 110, 120 are disposed in an open position, e.g., the jaw members 210, 220 are disposed in an open position, the blade 140 is prevented from being actuated as described above with respect to FIG. 1D. Upon initial closure of the shaft members 110, 120, the blade 140 may be actuated as described above with reference to FIG. 1E. Upon full actuation of the shaft members 110, 120, the blade is once against prevented from being actuated as described above with respect to FIG. 1F.

Figure 2A:
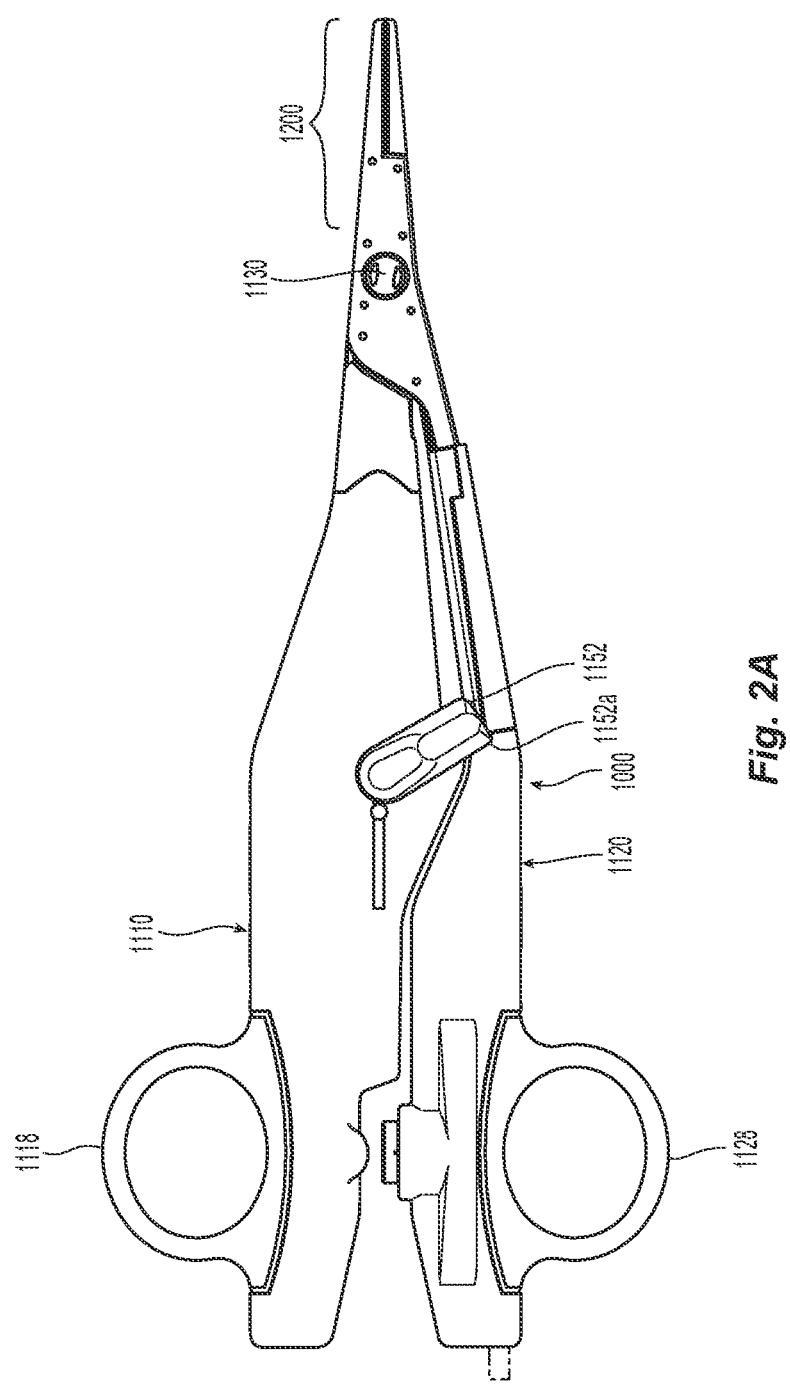
FIG. 2A is a side view of a first iteration of an electrosurgical forceps according to the present disclosure shown superimposed upon the forceps of FIG. 1A illustrating the same rotating trigger mechanism as the trigger mechanism of FIG. 1A shown overhanging a bottom shaft of the presently disclosed forceps.

FIG. 2A shows another embodiment of a forceps 1000 according to the present disclosure. Forceps 1000 is shown for illustrative purposes and includes opposing shafts 1110 and 1120 including an end effector assembly 1200 disposed at a distal end thereof. Shafts 1110 and 1120 are moveable via handles 1118, 1128 about a pivot 1130 to open and close the end effector assembly 1200. A trigger 1152 is disposed on shaft 1110 and is rotatable to deploy a knife (not shown) for cutting tissue much in the same fashion as described above with respect to forceps 100 of FIGS. 1A-1F. Forceps 1000 is shown superimposed atop the frame of forceps 100 to illustrate how a distal end 1152a of trigger 1152 projects beyond the periphery of shaft 1120 when disposed in an unactuated condition. As can be appreciated, designing a forceps in which the trigger projects from beyond the periphery of the shaft frame is not desirous.

Figure 2B:
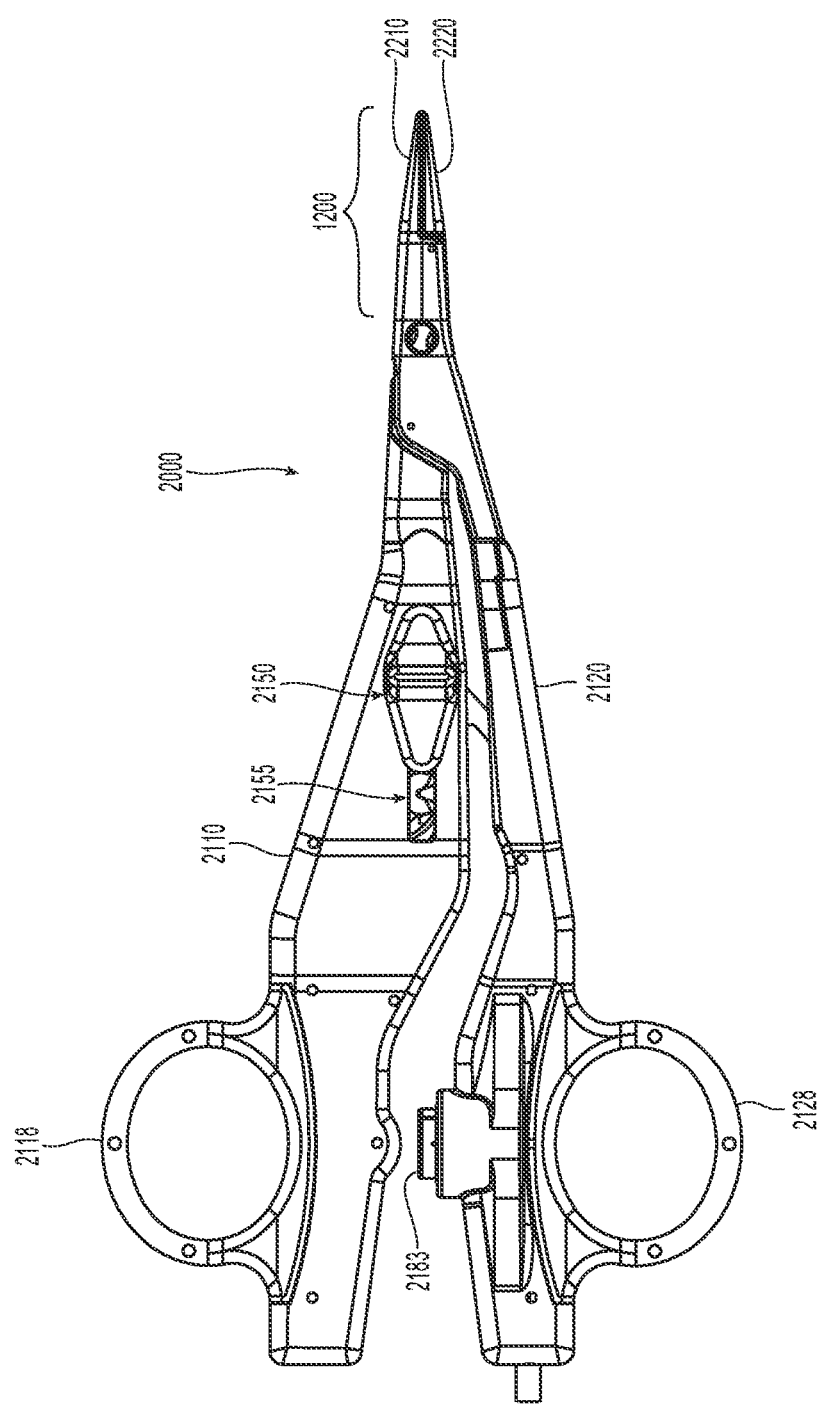
FIG. 2B is a side view of a second iteration of the electrosurgical forceps of FIG. 2A showing a linear trigger mechanism prior to actuation thereof.
Figure 2C:
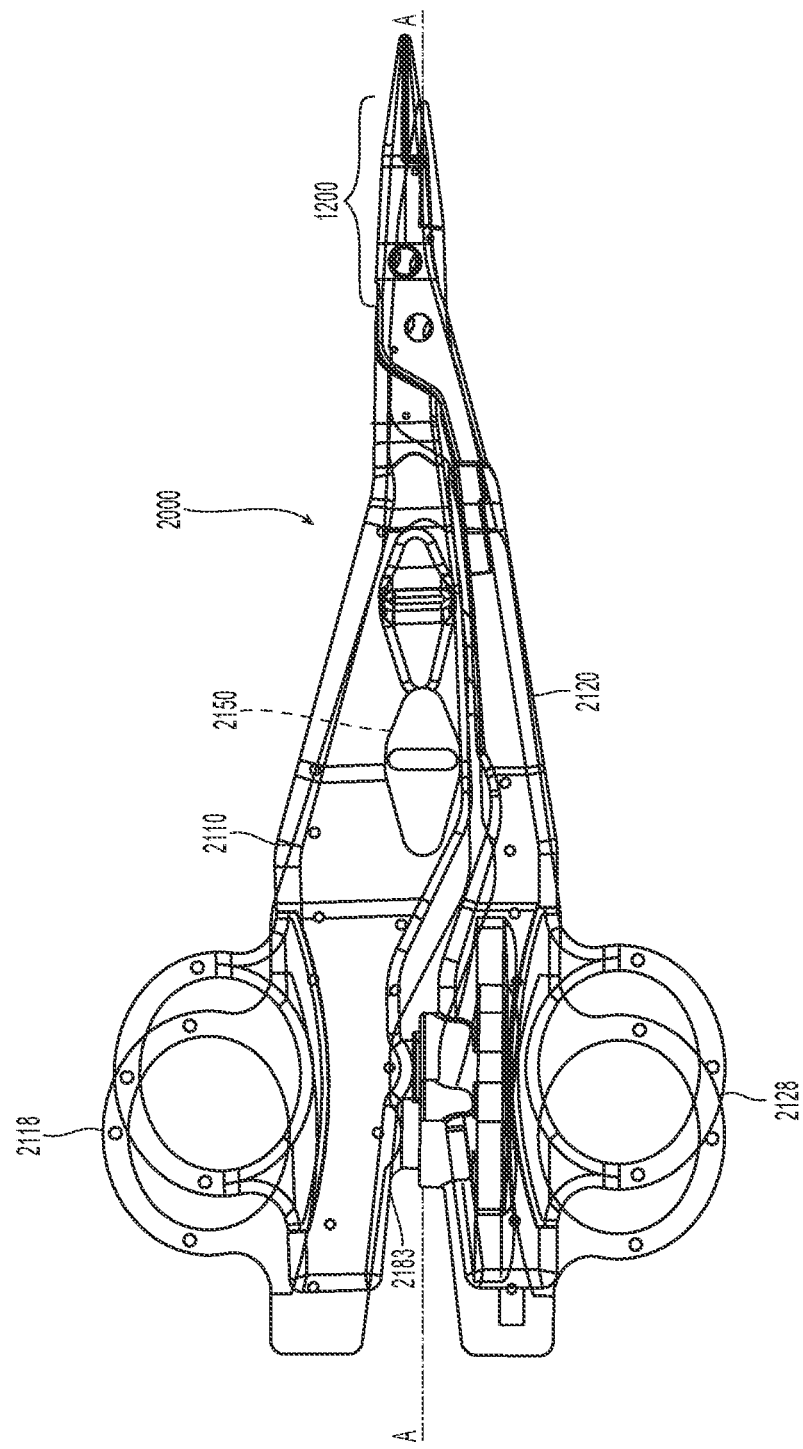
FIG. 2C is a side view of the electrosurgical forceps of FIG. 2B after actuation of a trigger thereof.

FIGS. 2B-2C show a lower profile, linear trigger design which is configured to inhibit the trigger from catching on the surgeon, patient, or on nearby objections during use and/or as forceps 2000 is inserted and withdrawn from the surgical site. More particularly, FIGS. 2B-2C show forceps 2000 having trigger 2150 that is actuated linearly along longitudinal axis "A-A" defined between shafts 2110, 2120 to advance a knife (not shown, but see knife 140) through tissue disposed between jaw members 2210, 2220 of end effector assembly 2200. As such, the trigger 2150 does not extend beyond the periphery of either shaft 2110, 2120 during the range of linear motion.

It is important to note that the various previously-described components are not described with reference to the remaining figures for the purposes of brevity and only those components necessary for each figure are described, however, it is intended that the former components or variations thereof may be used interchangeably with the remaining figures.

Referring back to FIGS. 2B-2C, FIG. 2B shows the linear trigger 2150 in an un-actuated position wherein the knife (not shown, but see knife 140) is disposed in a retracted position within a knife channel (not shown) defined between the jaw members 2210, 2220. In this position, a trigger channel 2155 is exposed. FIG. 2C shows the trigger 2150 in a proximal, actuated position to deploy the knife between jaw members 2210, 2220 to cut tissue. In this position, the trigger 2150 covers the trigger channel 2155 to reduce the chances of pinching a surgical glove or finger during repeated actuation. Trigger 2150 is symmetric on both sides of shaft 2110 allowing actuation by right or left-handed surgeons.

With the reduced profile of the forceps 2000, the internal working components of the knife deployment mechanism need to be slightly modified compared to the knife deployment mechanisms described above. Various types of deployment mechanism are envisioned and can generally be classified as linkage-type deployment mechanisms as shown in FIGS. 3A-3D and gear-like deployment mechanisms as shown in FIGS. 4A-4D.

Figure 3A:
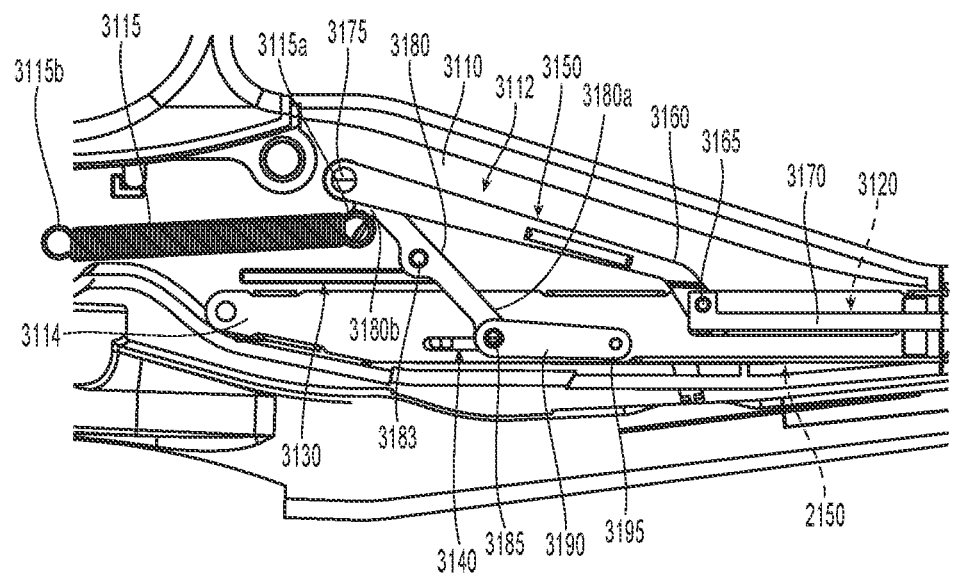
FIG. 3A is a partial, front perspective view of the forceps of FIG. 2B showing the internal components of a link-driven knife deployment mechanism according to the present disclosure.
Figure 3B:
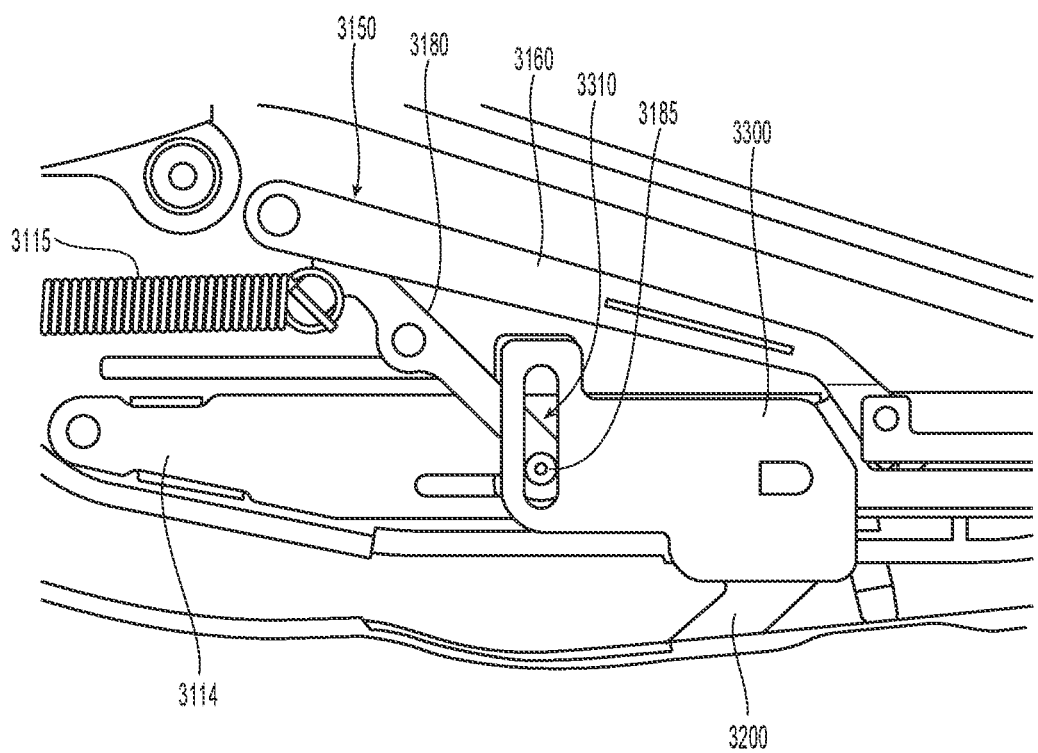
FIG. 3B is a side view of the forceps shown in FIG. 3A including a trigger carrier disposed atop the link-driven knife deployment mechanism according to the present disclosure.

Referring initially to FIGS. 3A-3B, a linkage-type knife deployment mechanism 3150 is shown and includes a knife carrier 3170, a series of linkages 3160, 3180, 3190 and a knife return spring 3115 that cooperate to smoothly advance the knife (not shown) in a linear motion upon actuation of trigger 2150 (FIGS. 2B-2C). More particularly, trigger 2150 connects to link 3190 via pin 3195 which, in turn, operably connects to crank link 3180 via pivot 3185. Pivot 3185 is configured to slide linearly in slot 3140 defined in knife support 3114. Crank link 3180 is operably connected to link 3160 via pivot 3175 which is supported within arcuate channel 3112 defined within shaft 3110. Link 3160 is operably connected to knife carrier 3170 via pin 3165. Pin 3165 is configured to translate knife carrier 3170 within slot 3120 defined in a distal end of knife support 3114. Knife support 3114 is, in turn, operably connected to knife (not shown, but see knife 140).

One end 3115a of knife return spring 3115 connects to crank link 3180 proximate link 3160 and moves concurrently therewith upon actuation of trigger 2150. The other end 3115b of spring 3115 is secured to shaft 3110.

The linkage design with a linear trigger 2150 allows the forceps 2000 height to decrease, requiring less housing constraints while maintaining a similar mechanical advantage to previous designs.

In use, when trigger 2150 is actuated (pulled back proximally), pin 3195 moves link 3190 proximally which, in turn, moves pivot 3185 proximally within slot 3140. As pivot 3185 moves proximally within slot 3140, a distal end 3180a of crank link 3180 moves therewith causing pin 3183 to move proximally and rotate clockwise within slot 3130 which, in turn, forces the proximal end 3180b of crank link 3180 distally. Movement of proximal end 3180b of crank link 3180 distally rotates link 3160 distally within arcuate slot 3112 against the bias of return spring 3115. Distal movement of link 3160 forces knife carrier 3170 distally within slot 3120 to advance knife (not shown) through tissue.

Once actuated, the force of spring 3115 reverses the motion of the knife carrier 3170 and links 3160, 3180, 3190 to return the trigger 2150 distally back to an unactuated position. As explained in more detail below, if the knife (not shown) is stuck in the knife channel between jaw members 2210, 2120 or on tissue, a knife kickout may be used to force the knife proximally as the shafts 2110, 2120 are opened (See FIGS. 6A-8B).

FIG. 3B shows another embodiment of the knife deployment mechanism 3150 for use with forceps 2000 which includes a trigger carrier 3300 that operably connects to the trigger 2150. Trigger carrier 3300 includes a cam slot 3310 defined therein that resides in general perpendicular registration with slot 3140 in knife carrier 3114 and that is configured to slidingly receive pivot 3185 therein. Upon actuation of the trigger 2150, trigger carrier 3300 is moved proximally and the pivot 3185 rides along the cam slot 3310 in a general perpendicular direction. Utilizing the cam slot 3310 allows for smoother and more consistent actuation of trigger 2150.

Figure 3C:
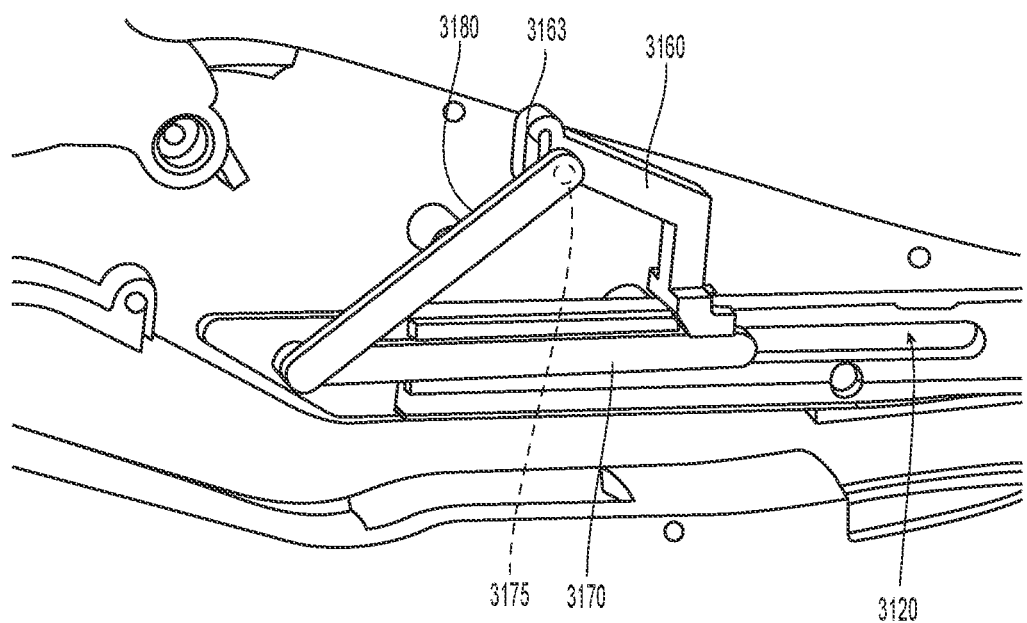
FIG. 3C is a rear perspective view of another embodiment of a link-driven knife deployment mechanism according to the present disclosure.

FIG. 3C shows another embodiment of the knife deployment mechanism 3150 for use with forceps 2000 which includes a guide slot 3163 defined within a proximal end of link 3160 that allows pivot 3175 to ride therein during actuation of trigger 2150. Upon actuation of the trigger 2150, link 3170 is moved proximally to pivot link crank 3180 distally which, in turn, forces link 3160 distally to advance knife (not shown). Utilizing the guide slot 3163 allows for smoother and more consistent actuation of the trigger 2150 and knife through their range of motion.

Figure 3D:
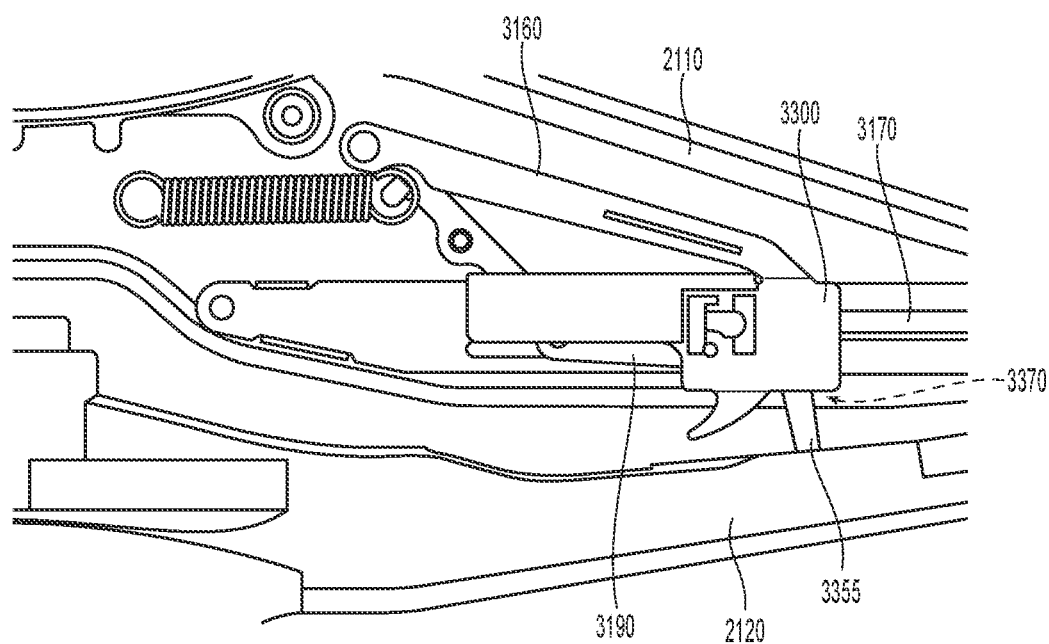
FIG. 3D is a side view of another embodiment of a link-driven knife deployment mechanism according to the present disclosure.

FIG. 3D shows another embodiment of the knife deployment mechanism 3150 for use with forceps 2000 which includes a knife lockout mechanism 3370 (shown in phantom) for use with the knife deployment mechanism 3150. Knife lockout mechanism 3370 is similar to knife lockout 170 of FIGS. 1D-1F and, as such, is only described in brief detail herein. Knife lockout mechanism 3370 includes a flange 3355 disposed in operative engagement with the knife carrier 3170 and depending therefrom. When the trigger 2150 is in an unactuated position, flange 3355 is configured to project downwardly relative thereto in alignment with shaft 2120 of forceps 2000. Upon closing of the handles 2118, 2128, the flange 3355 abuts against shaft 2120 and is forced inwardly toward shaft 2110 to disengage the flange 3355 from the knife carrier 3170. Once disengaged, the trigger 2150 is free to actuate the knife (not shown). When the trigger 2150 is returned to an unactuated position and the handles 2118, 2128 are moved away from one another, the flange 3355 re-engages the knife carrier 3170 to prevent translation of the knife.

Figure 4A:
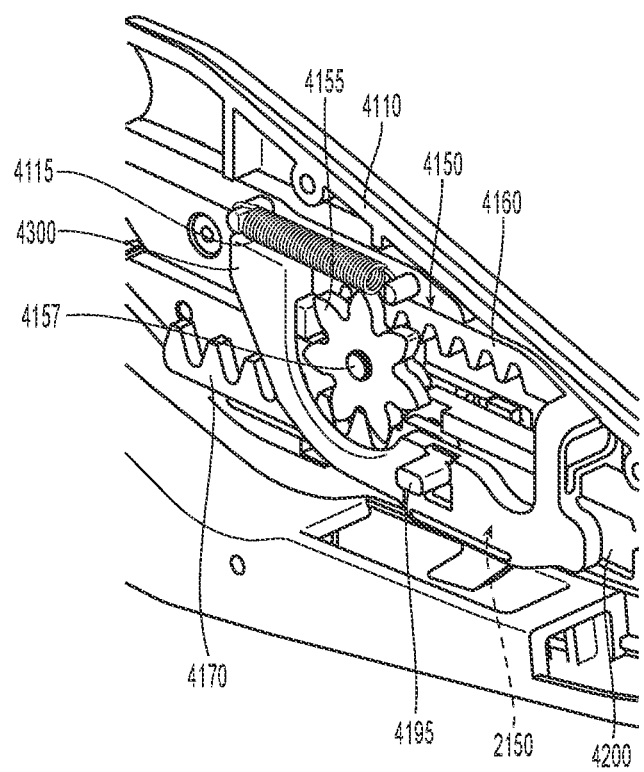
FIG. 4A is a partial, front perspective view of the forceps of FIG. 2B showing the internal components of a rack and gear-driven knife deployment mechanism according to the present disclosure.
Figure 4B:
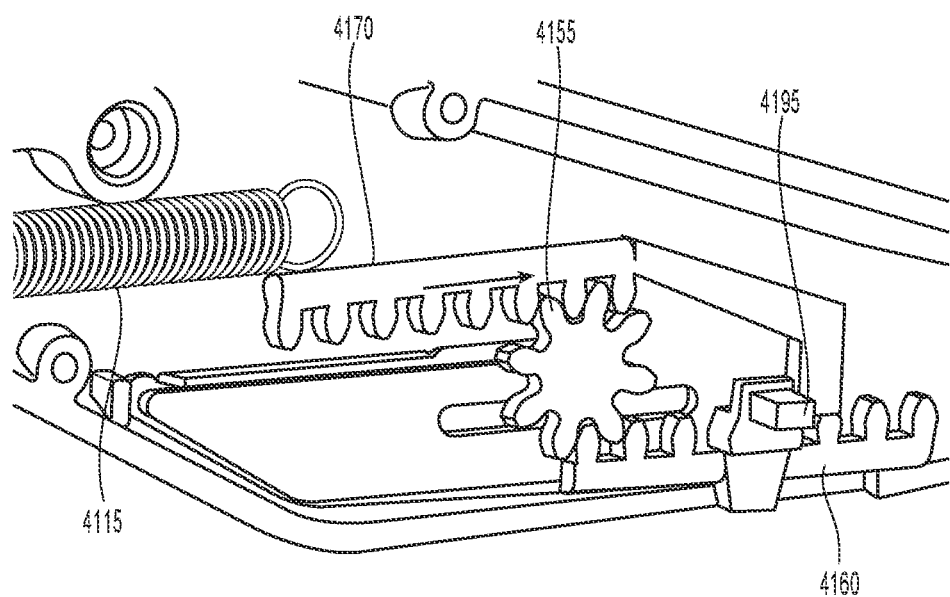
FIG. 4B is a rear perspective view of another embodiment of a gear-driven knife deployment mechanism according to the present disclosure.

Referring to FIGS. 4A and 4B, a gear-type knife deployment mechanism 4150 is shown and includes a blade rack 4170, a trigger rack 4160 and a gear 4155 disposed therebetween. Gear 4155 is configured to reverse direction between the two racks 4160, 4170 and may also be utilized to amplify overall force or distance therebetween. Blade rack 4170 is operably coupled to the trigger 2150 (FIG. 2B) via a trigger carrier 4300, which, in turn, includes one or more pins 4195 or other mechanical interfaces that engage the trigger 2150 directly such that movement of the trigger 2150 correspondingly moves the blade rack 4170.

Gear 4155 is mounted about pin 4157 to shaft 4110 and between racks 4160, 4170. Movement of one rack, e.g., rack 4170 causes the other rack, e.g., rack 4160, to move in the opposite direction. Rack 4160 is operably couple to the knife carrier 4200. As such, proximal movement of the trigger 2150 is converted to distal movement of the knife (not shown).

FIG. 4B shows an alternative setup of a gear-type knife deployment mechanism 4150 showing slightly modified blade and trigger racks 4170, 4160 for actuating the knife and return spring 4115 for facilitating the return of the knife. Return spring 4115 is operably coupled to the blade rack 4170 but may be coupled to either rack 4160, 4170 depending upon a particular purpose.

Figure 4C:
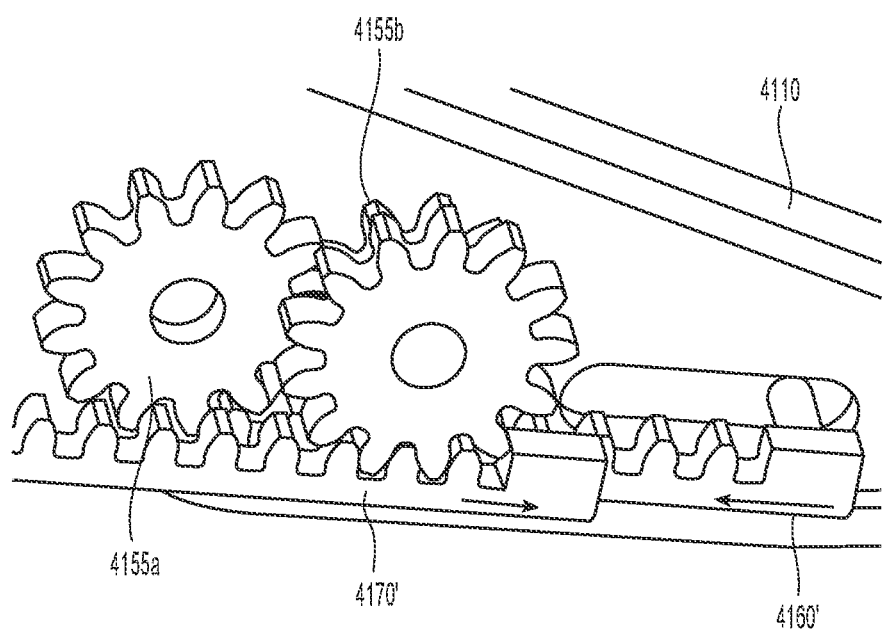
FIG. 4C is a top perspective view of another embodiment of a gear-driven knife deployment mechanism according to the present disclosure.

FIG. 4C shows yet another embodiment of a gear-type knife deployment mechanism 4150' showing slightly modified blade and trigger racks 4170', 4160' and two gears for actuating the knife (not shown). More particularly, a single gear 4155*a* is operably associated with trigger rack 4160' and a compound gear 4155*b* is operably associated with blade rack 4170'. Compound gear 4155*b* allows the two gears 4155*a*, 4155*b* to align in general vertical registry while still providing the same reversing effect between the trigger 2150 and knife deployment. As can be appreciated, this may save valuable real estate within the shaft 4110 for additional components or a reduced profile.

Figure 4D:
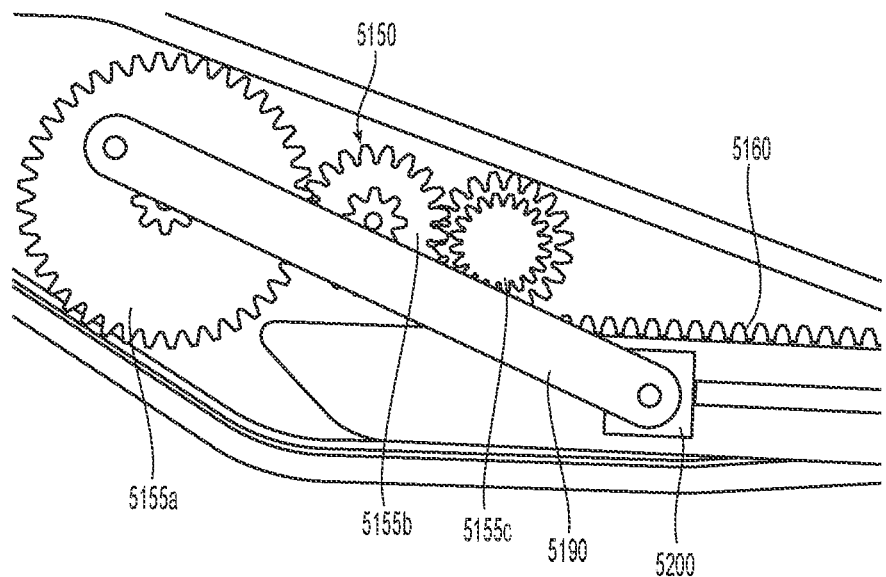
FIG. 4D is a side view of another embodiment of a compound gear-driven knife deployment mechanism according to the present disclosure.

FIG. 4D shows another embodiment of a combination gear and lever-type knife deployment mechanism 5150 having a trigger rack 5160 operably coupled to a compound gear 5155*c*, multiple single gears 5155*a*, 5155*b*, a knife link 5190, and a knife carrier 5200. As can be appreciated, this combination deployment mechanism 5150 can be configured to provide mechanical advantages for amplifying overall force applied to the knife or distance the knife travels with trigger 2150 actuation.

Figure 5A:
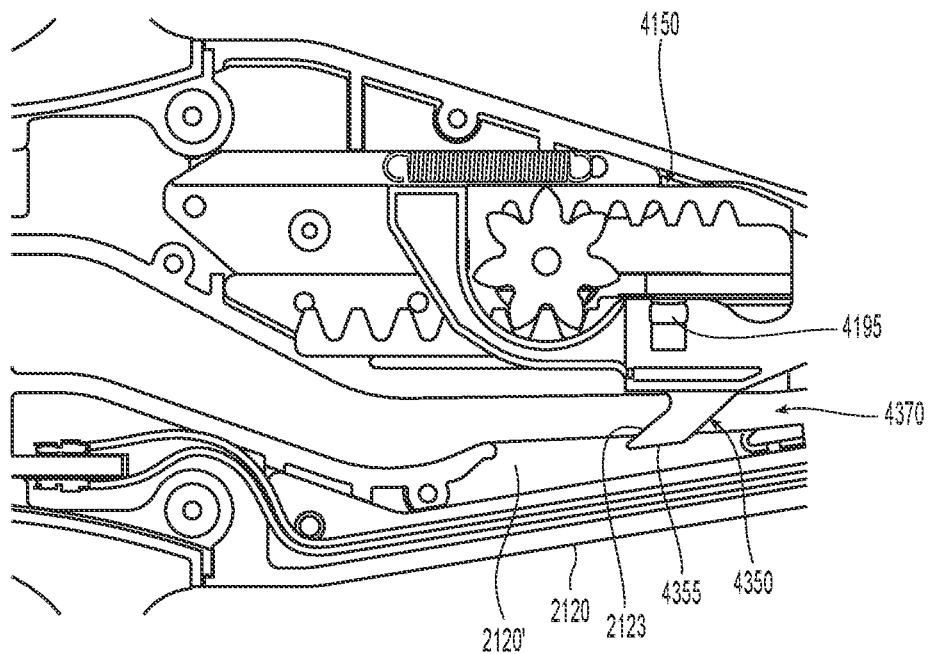
FIG. 5A is a side perspective view of the forceps and gear-driven knife deployment mechanisms of FIG. 4A showing a knife kickout according to the present disclosure.

FIG. 5A shows a knife kickout mechanism 4370 for use with the knife deployment mechanism 4150 of FIG. 4A. Knife kickout mechanism 4370 includes a flange 4355 disposed in operative engagement with the knife carrier 4200 (See FIG. 4A) and depending therefrom. When the trigger 2150 is in an unactuated position, flange 4355 is configured to project downwardly relative thereto in alignment with shaft 2120 of forceps 2000. Upon closing of the handles 2118, 2128, the flange 4355 is received within a slot defined in the shaft 2110 and is forced inwardly toward a kickout ramp 2121 (See FIG. 6A). When the trigger 2150 is returned to an unactuated position and the handles 2118, 2128 are moved away from one another, the flange 4355 engages the kickout ramp 212 to urge the knife carrier 4200 forward facilitating knife carrier 4200 return.

Figure 5B:
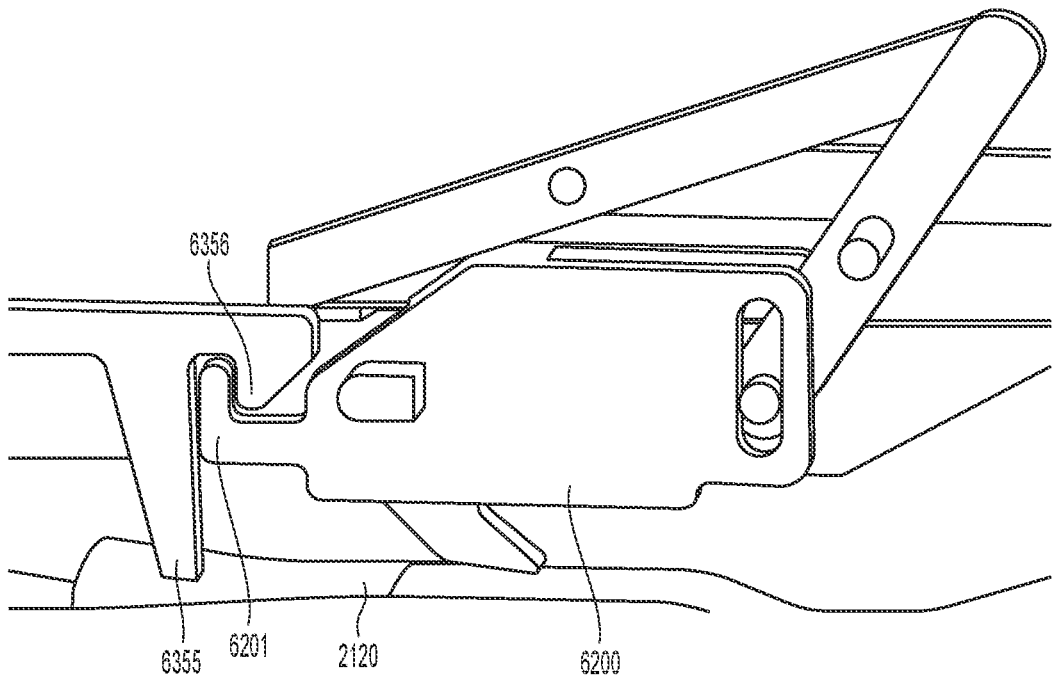
FIG. 5B is a side perspective view of another embodiment of a knife kickout according to the present disclosure.

FIG. 5B shows a knife lockout mechanism 6370 for use with the knife deployment mechanism similar to those shown in FIGS. 3A-3D. Knife lockout mechanism 6370 is similar to knife lockout 170 of FIGS. 1D-1F and as such, is only described in brief detail herein. Knife lockout mechanism 6370 includes a flange 6355 disposed in rotational engagement with the knife carrier 6200. When the trigger 2150 is in an unactuated position, flange 6355 is configured to project downwardly relative thereto in alignment with shaft 2120 of forceps 2000. Upon closing of the handles 2118, 2128, the flange 6355 abuts against shaft 2120 and is forced inwardly toward shaft 2110 (See FIGS. 2B and 2C) and a distal end 6356 of the flange 6355 rotates out of engagement with a proximal hook portion 6201 of the knife carrier 6200. Once disengaged, the trigger 2150 is free to actuate the knife (not shown). When the trigger 2150 is returned to an unactuated position and the handles 2118, 2128 are moved away from one another, the distal end 6356 of the flange 6355 re-engages the hook portion 6201 of the knife carrier 6200 to prevent translation of the knife.

Referring to FIGS. 6A-8B, various embodiments of a knife kickout are envisioned. The described knife kickout mechanisms are configured to work with many of the aforedescribed forceps and internal components thereof, and as such, only those components necessary for an accurate understanding of the kickout are described in detail herein.

Figure 6A:
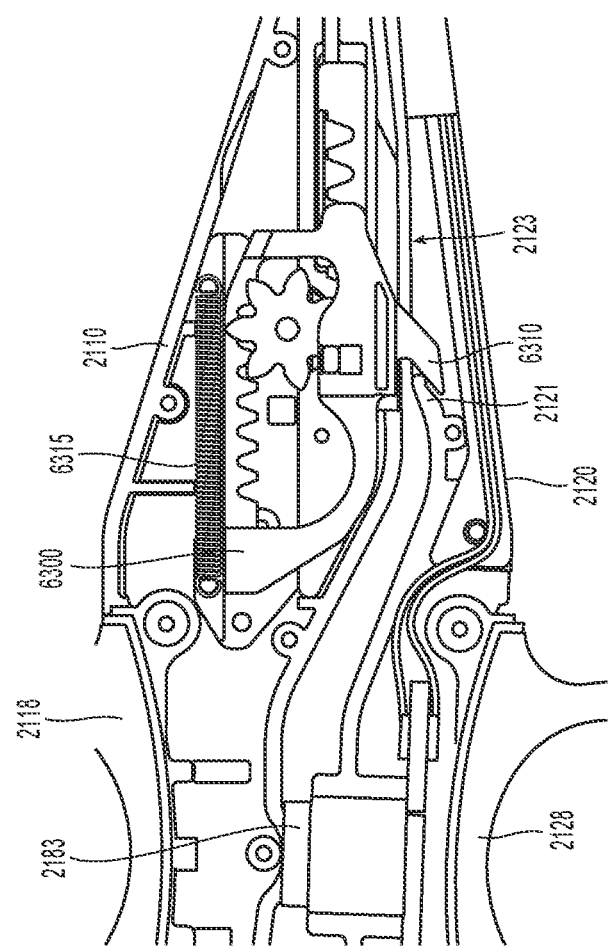
FIGS. 6A-6B are side views of the knife kickout of FIG. 5A illustrating operational movement thereof.
Figure 6B:
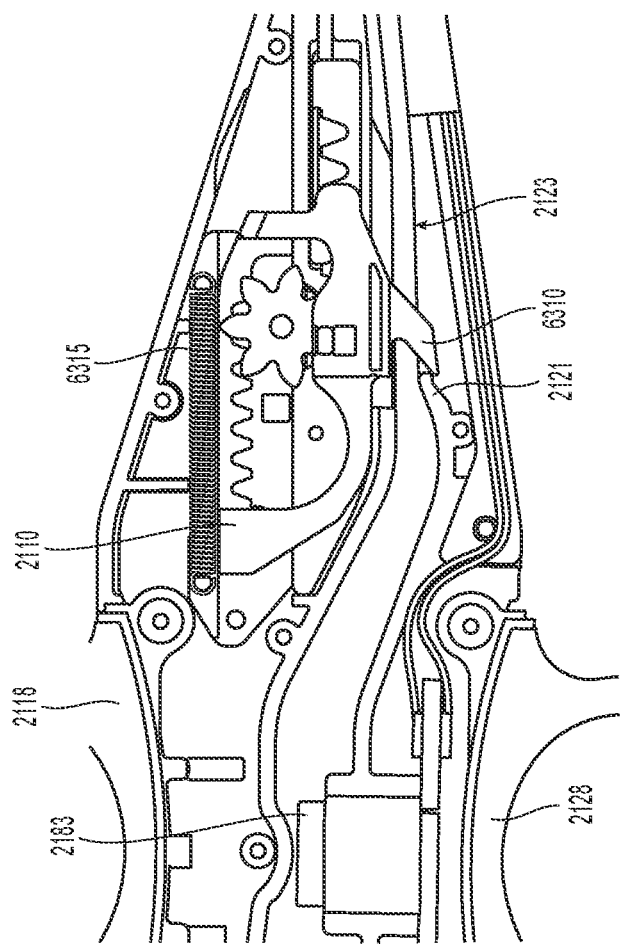

FIGS. 6A-6B show one embodiment of a knife kickout 6310 for use with trigger carrier 6300. Knife kickout 6310 is configured to depend from trigger carrier 6300 and align in vertical registration with an elongated kickout slot 2123 defined within shaft 2120. Shaft 2120 also includes a kickout ramp 2121 defined at a proximal-most portion of the kickout slot 2123. Upon approximation of handles 2118, 2128 of forceps 2000 (FIGS. 2A-2C), shafts 2110, 2120 are urged into close abutment with one another to either allow actuation of the knife (not shown) via trigger 2150 and/or activation of electrical energy via switch 2183.

As the trigger carrier 6300 is actuated (proximally), the kickout 6310 rides within slot 2123 of shaft 2120 into abutment with kickout ramp 2121. Typically, upon release of the trigger 2150, trigger carrier 6300 is supposed to automatically return to a distal-most position under the bias of knife return spring 6315. If the knife (not shown) gets caught in the knife channel disposed between jaw members 2210, 2220 or gets caught on tissue, the bias of the knife return spring 6315 may not be enough and the knife may remain in a deployed position.

In this instance, and in order to kick out the knife and get it moving proximally out of the knife channels, the user simply begins to open the forceps 2000 causing the shafts 2110, 2120 to move relative to one another and causing the kickout ramp 2121 to essentially "kick" the knife kickout 6310 forward as the handles 2118, 2128 open. Forward motion of the knife kickout 6310, in turn, forces the trigger carrier 6300 forward and, thus, forces the knife proximally.

Figure 7A:
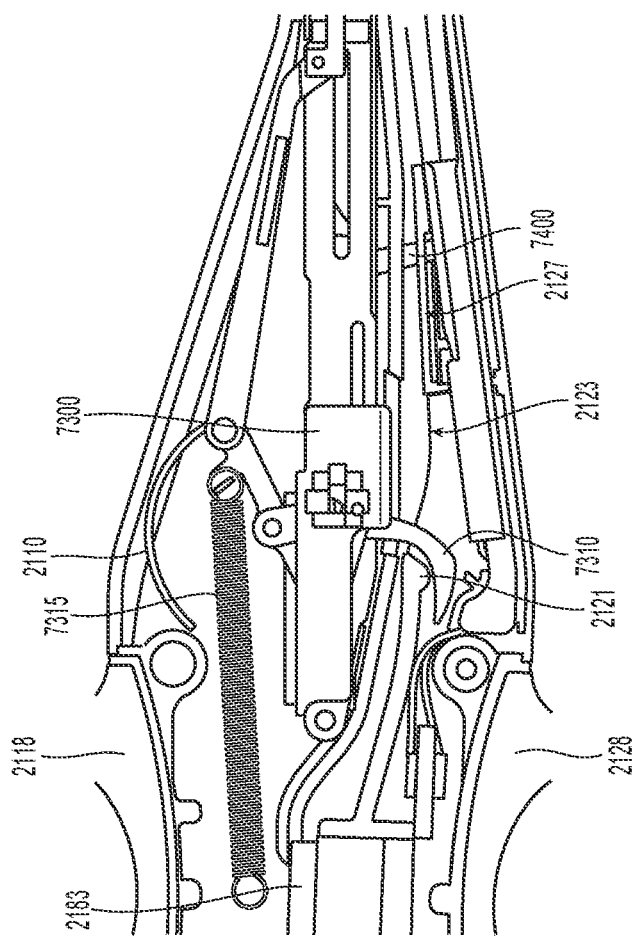
FIGS. 7A-7B are side views of another embodiment of a knife kickout according to the present disclosure illustrating operational movement thereof.
Figure 7B:
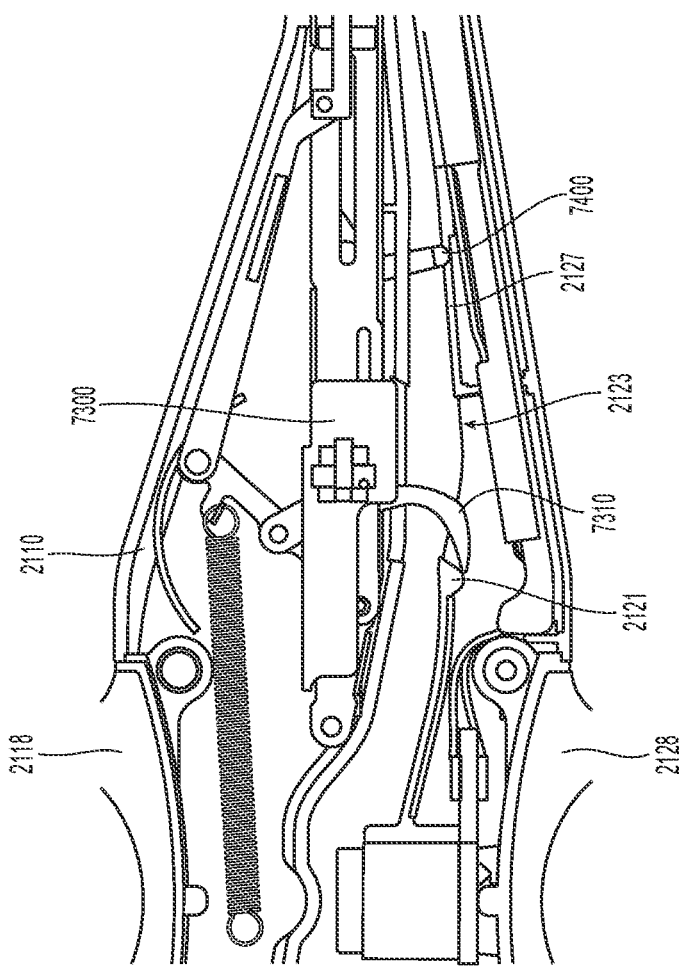

FIGS. 7A-7B show another embodiment of a knife kickout 7310 for use with trigger carrier 7300. Knife kickout 7310 is configured to depend from trigger carrier 7300 and align in vertical registration with an elongated kickout slot 2123 defined within shaft 2120. Shaft 2120 also includes a kickout ramp 2121 defined at a proximal-most portion of the kickout slot 2123. Upon approximation of handles 2118, 2128 of forceps 2000 (FIGS. 2A-2C), shafts 2110, 2120 are urged into close abutment with one another to either allow actuation of the knife (not shown) via trigger 2150 and/or activation of electrical energy via switch 2183.

As the trigger carrier 7300 is actuated (proximally), the kickout 7310 rides within slot 2123 of shaft 2120 into abutment with kickout ramp 2121. Typically, upon release of the trigger 2150, trigger carrier 7300 is supposed to automatically return to a distal-most position under the bias of knife return spring 7315. If the knife (not shown) gets caught in the knife channel disposed between jaw members 2210, 2220 or gets caught on tissue, the bias of the knife return spring 7315 may not be enough and the knife may remain in a deployed position.

In this instance, and in order to kick out the knife and get it moving proximally out of the knife channels, the user simply begins to open the forceps 2000 causing the shafts 2110, 2120 to move relative to one another and causing the kickout ramp 2121 to essentially "kick" the knife kickout 7310 forward as the handles 2118, 2128 open. Forward motion of the knife kickout 7310, in turn, forces the trigger carrier 7300 forward and, thus, forces the knife proximally.

Figure 8A:
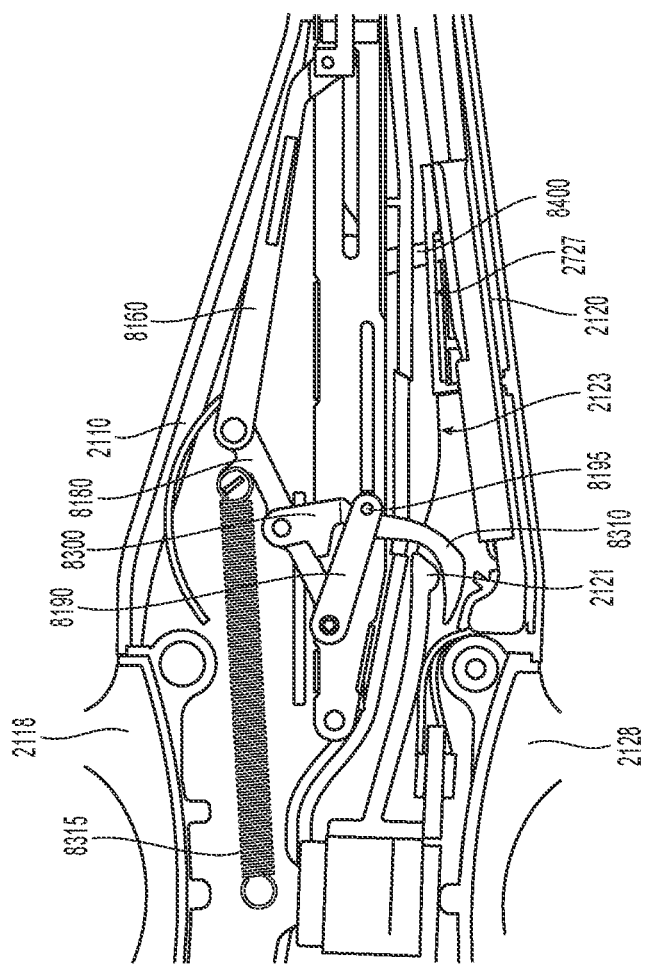
FIGS. 8A-8B are side views of another embodiment of a knife kickout according to the present disclosure illustrating operational movement thereof.
Figure 8B:
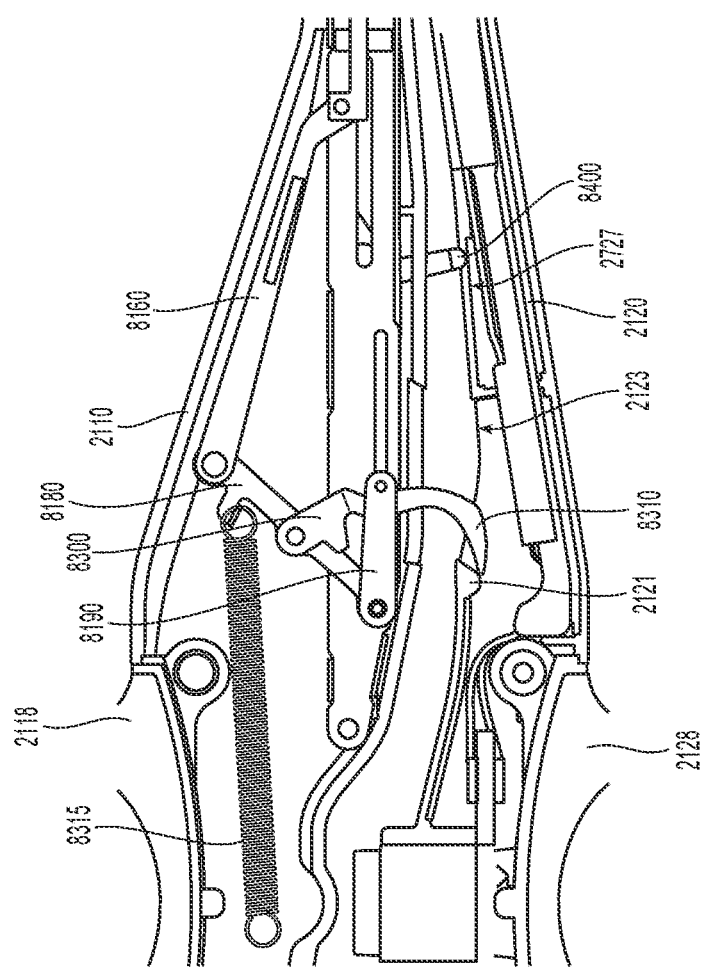

FIGS. 8A-8B show another embodiment of a knife kickout 8310 for use with kickout link 8300. Knife kickout 8310 is configured to depend from kickout link 8300 and align in vertical registration with an elongated kickout slot 2123 defined within shaft 2120. Shaft 2120 also includes a kickout ramp 2121 defined at a proximal-most portion of the kickout slot 2123. Upon approximation of handles 2118, 2128 of forceps 2000 (FIGS. 2A-2C), shafts 2110, 2120 are urged into close abutment with one another to either allow actuation of the knife (not shown) via trigger 2150 and/or activation of electrical energy via switch 2183. Kickout link 8300 is rotatingly engaged at one end to link 8180 and positioned proximally of pivot 8195 a distal end of link 8190 such that movement of link 8190 pulls kickout link 8300 proximally along therewith.

As mentioned above with respect to FIG. 3A, as the trigger 2150 is actuated, kickout link 8300 is actuated (proximally), the kickout 8310 rides within slot 2123 of shaft 2120 into abutment with kickout ramp 2121. Typically, upon release of the trigger 2150, kickout link 8300 is supposed to automatically return to a distal-most position under the bias of knife return spring 8315. If the knife (not shown) gets caught in the knife channel disposed between jaw members 2210, 2220 or gets caught on tissue, the bias of the knife return spring 8315 may not be enough and the knife may remain in a deployed position.

In this instance, and in order to kick out the knife and get it moving proximally out of the knife channels, the user simply begins to open the forceps 2000 causing the shafts 2110, 2120 to move relative to one another and causing the kickout ramp 2121 to essentially "kick" the knife kickout 8310 and link 8180 forward as the handles 2118, 2128 open. Forward motion of the knife kickout 8310, in turn, forces the kickout link 8300 and link 8180 forward and, thus, forces the knife proximally.

Figure 9:
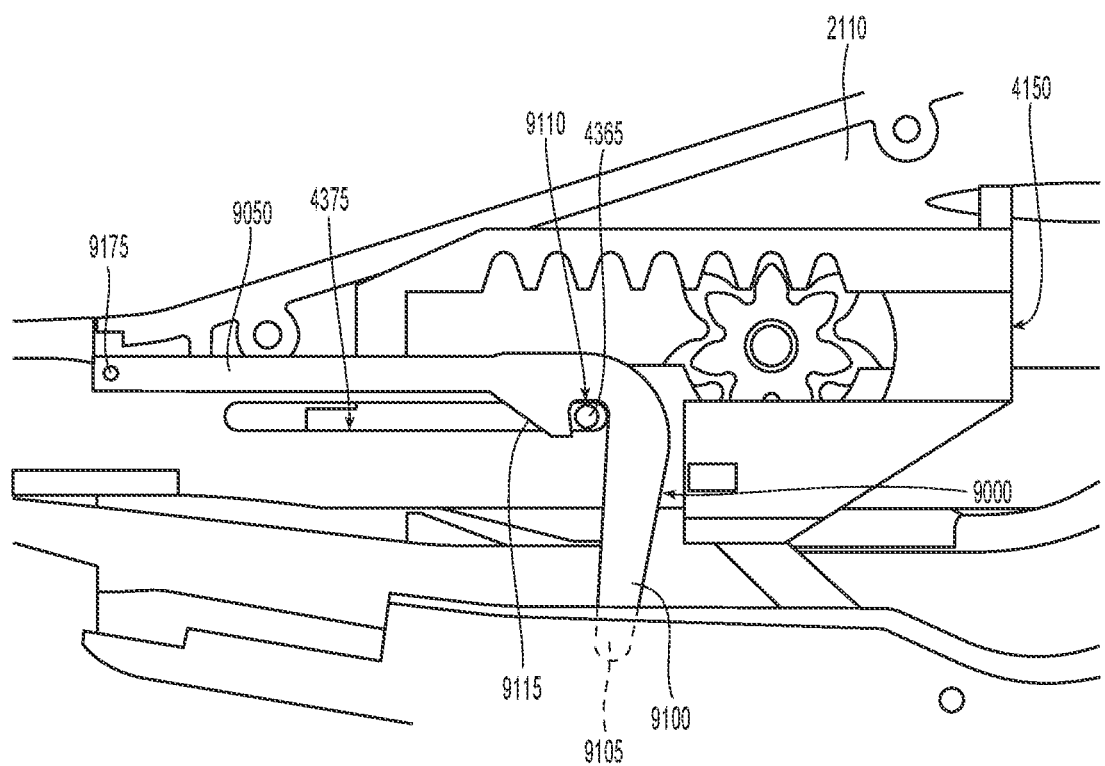
FIG. 9 is a side view of the knife lockout according to the present disclosure.
Figure 10:
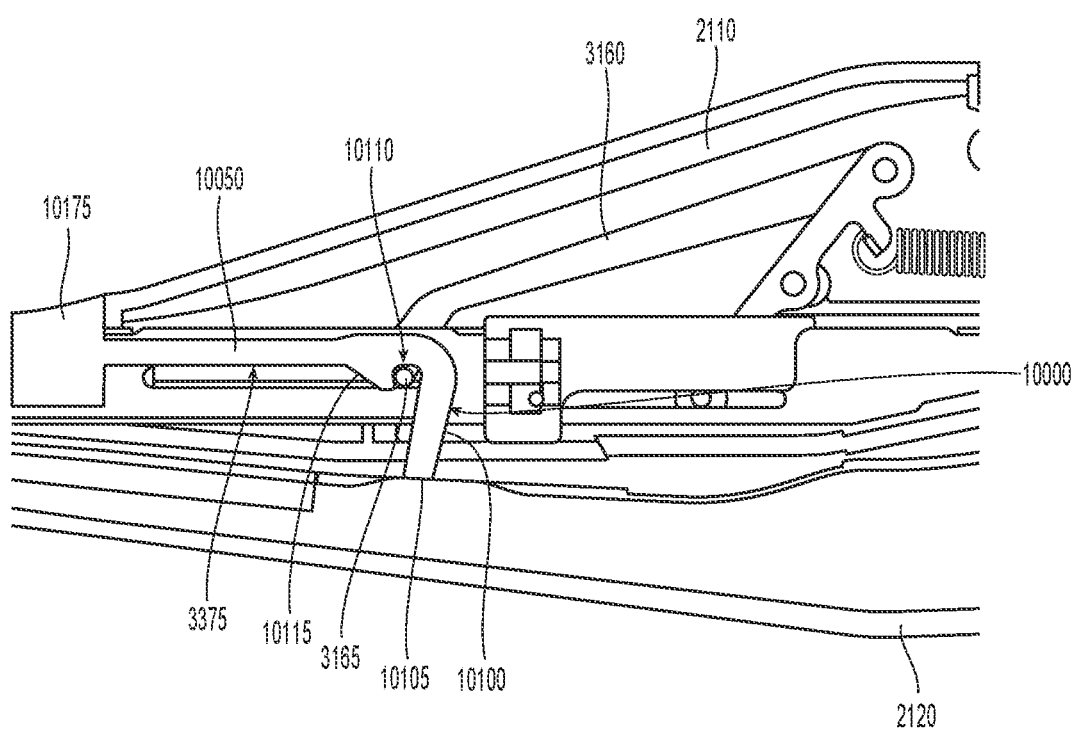
FIG. 10 is a side view of another embodiment of a knife lockout according to the present disclosure.
Figure 11:
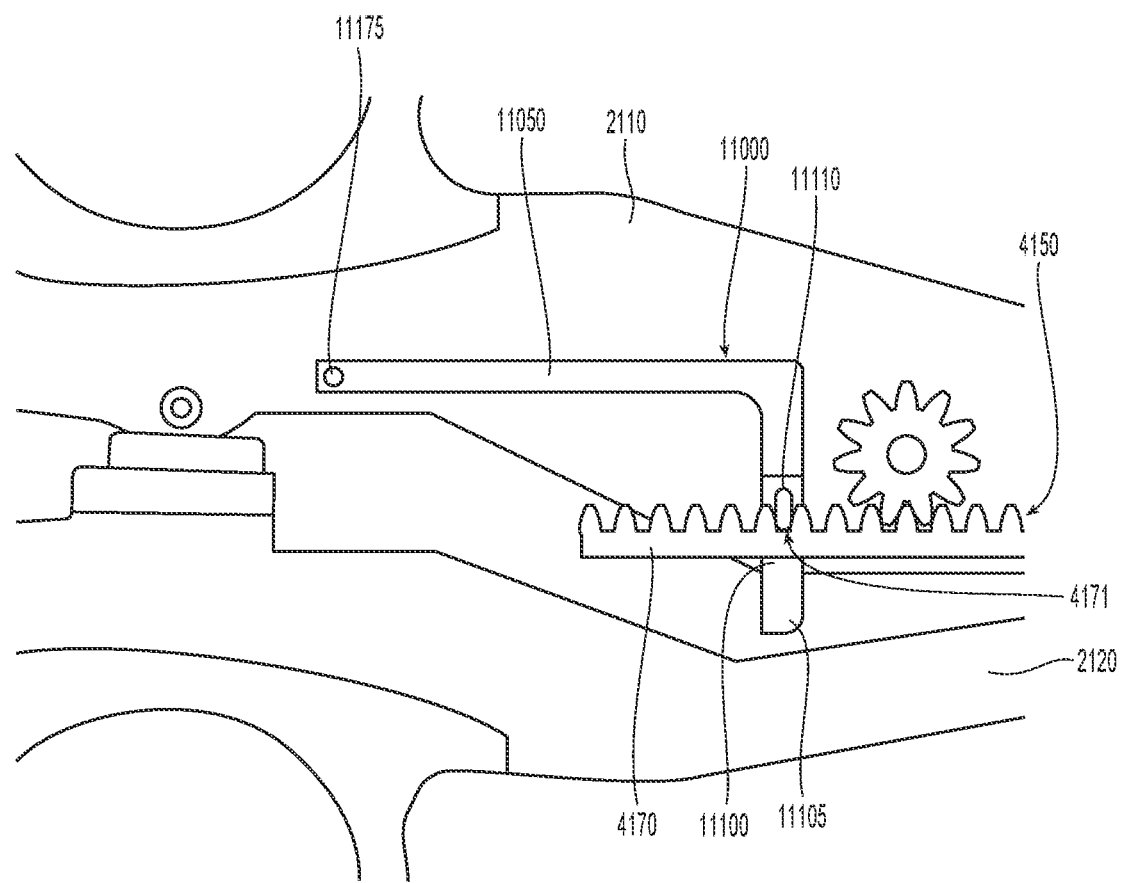
FIG. 11 is a side view of another embodiment of a knife lockout according to the present disclosure.

Referring to FIGS. 9-11, various embodiments of a knife lockout are envisioned. The described knife lockout mechanisms are configured to work with many of the aforedescribed forceps and internal components thereof, and as such, only those components necessary for an accurate understanding of the kickout are described in detail herein.

FIG. 9 shows one embodiment of a knife lockout 9000 for use with, for example, forceps 2000 and knife deployment mechanism 4150 described in FIG. 4A. Knife lockout 9000 is L-shaped and includes an elongated shaft 9050 connected at a distal end thereof to shaft 2110 by a flange pin 9175 and terminating at an opposite end thereof with a flange 9100 that depends in oppositional registry with shaft 2120. The distal end 9105 of flange 9100 is configured to abut shaft 2120 upon approximation of shaft members 2110, 2120 to force flange inwardly towards shaft 2110.

Knife deployment mechanism 4150 includes a locking pin 4365 operably engaged with trigger rack 4160 (see FIG. 4B) that is configured to ride within an elongated slot 4375 defined therein upon actuation of the knife deployment mechanism 4150. Flange 9100 includes a slot 9110 defined therein configured to seat locking pin 4365 therein to prevent actuation of the knife deployment mechanism 4150 when the shaft members 2110, 2120 are disposed in an open position.

In use, when the shaft members 2110, 2120 are disposed in an open position relative to one another, the locking pin 4365 is seated within slot 9110 preventing movement of the knife deployment mechanism 4150. When the shaft members 2110, 2120 are approximated, the distal end 9105 of flange 9100 abuts shaft 2120 forcing the flange 9100 towards shaft 2110 and causing the elongated shaft 9050 to flex about flange pin 9175. As a result, locking pin 4365 is unseated or disengaged from slot 9110 allowing actuation of the knife deployment mechanism 4150. Locking pin 4365 rides along elongated slot 4375 during actuation. Flange pin 9175 is anchored to shaft 2110 to bias flange 9100. A conventional spring, e.g., torsion spring (not shown), may also be utilized for this purpose.

After actuation of the knife deployment mechanism 4150, the knife deployment mechanism 4150 and the trigger 2150 are released and returned under the bias of the knife return spring 4115 (See FIG. 4A). As a result thereof, locking pin 4365 returns along elongated slot 4375 to its unactuated position. Upon return, the locking pin 4365 engages ramp a 9115 disposed distally of slot 9110 which forces flange 9100 inwardly relative to shaft 2110 to allow the locking pin 4365 to reseat within slot 9110 re-locking the knife deployment mechanism 4150 and preventing movement thereof. Any type of conventional spring (not shown) may also be utilized for this purpose.

FIG. 10 shows another embodiment of a knife lockout 10000 for use with, for example, forceps 2000 and knife deployment mechanism 3150 described in FIG. 3A. Knife lockout 10000 is L-shaped and includes an elongated shaft 10050 connected at a distal end thereof to shaft 2110 by a sleeve 10175 and terminating at an opposite end thereof with a flange 10100 that depends in oppositional registry with shaft 2120. The distal end 10105 of flange 10100 is configured to abut shaft 2120 upon approximation of shaft members 2110, 2120 to force flange inwardly towards shaft 2110.

Knife deployment mechanism 3150 includes a locking pin 3165 that operably engages link 3160 and knife carrier 3170 and that is configured to ride within an elongated slot 3375 defined in knife carrier 3170 upon actuation of the knife deployment mechanism 3150. Flange 10100 includes a slot 10110 defined therein configured to seat locking pin 3165 therein to prevent actuation of the knife deployment mechanism 3150 when the shaft members 2110, 2120 are disposed in an open position.

In use, when the shaft members 2110, 2120 are disposed in an open position relative to one another, the locking pin 3165 is seated within slot 10110 preventing movement of the knife deployment mechanism 3150. When the shaft members 2110, 2120 are approximated, the distal end 10105 of flange 10100 abuts shaft 2120 forcing the flange 10100 towards shaft 2110 and causing the elongated shaft 10050 to flex about sleeve 10175. As a result, locking pin 3165 is unseated or disengaged from slot 10110 allowing actuation of the knife deployment mechanism 3150. Locking pin 3165 rides along elongated slot 3375 during actuation.

After actuation of the knife deployment mechanism 3150, the knife deployment mechanism 3150 and the trigger 2150 are released and returned under the bias of the knife return spring 3115 (See FIG. 3A). As a result thereof, locking pin 3165 returns along elongated slot 3375 to its unactuated position. Upon return, the locking pin 3165 engages ramp a 10115 disposed distally of slot 10110 which forces flange 10100 inwardly relative to shaft 2110 to allow the locking pin 3165 to reseat within slot 10110 re-locking the knife deployment mechanism 3150 and preventing movement thereof.

FIG. 11 shows another embodiment of a knife lockout 11000 for use with, for example, forceps 2000 and knife deployment mechanism 4150 described in FIG. 4A. Knife lockout 11000 is L-shaped and includes an elongated shaft 11050 connected at a proximal end thereof to shaft 2110 by a flange pin 11175 and terminating at an opposite end thereof with a flange 11100 that depends in oppositional registry with shaft 2120. The distal end 11105 of flange 11100 is configured to abut shaft 2120 upon approximation of shaft members 2110, 2120 to force flange inwardly towards shaft 2110.

Flange 11100 includes a boss 11110 disposed thereon therein configured to seat within a gear slot 4171 defined in gear rack 4170 to prevent actuation of the knife deployment mechanism 4150 when the shaft members 2110, 2120 are disposed in an open position.

In use, when the shaft members 2110, 2120 are disposed in an open position relative to one another, the boss 11110 is seated within gear slot 4171 preventing movement of the knife deployment mechanism 4150. When the shaft members 2110, 2120 are approximated, the distal end 11105 of flange 11100 abuts shaft 2120 forcing the flange 11100 towards shaft 2110 and causing the elongated shaft 11050 to rotate about flange pin 11175. As a result, boss 11110 is unseated or disengaged from gear slot 4171 allowing actuation of the knife deployment mechanism 4150. Boss 11110 remains out of the way during movement of the opposing racks 4170, 4160 (FIG. 4A).

After actuation of the knife deployment mechanism 4150, the knife deployment mechanism 4150 and the trigger 2150 are released and returned under the bias of the knife return spring 4115 (See FIG. 4A). As a result thereof, boss 11110 re-engages gear slot 4171 re-locking the knife deployment mechanism 4150 and preventing movement thereof.

FIGS. 12-14G show a forceps 20000 that includes another embodiment of a knife kickout mechanism 20302 configured to facilitate returning the knife (not shown) after cutting. More particularly and unlike the previously described embodiments, knife kickout mechanism 20302 is configured to move independently to facilitate knife return after cutting and is not dependent on the rotational path of the opposing shaft members 20110, 20120.

Figure 12A:
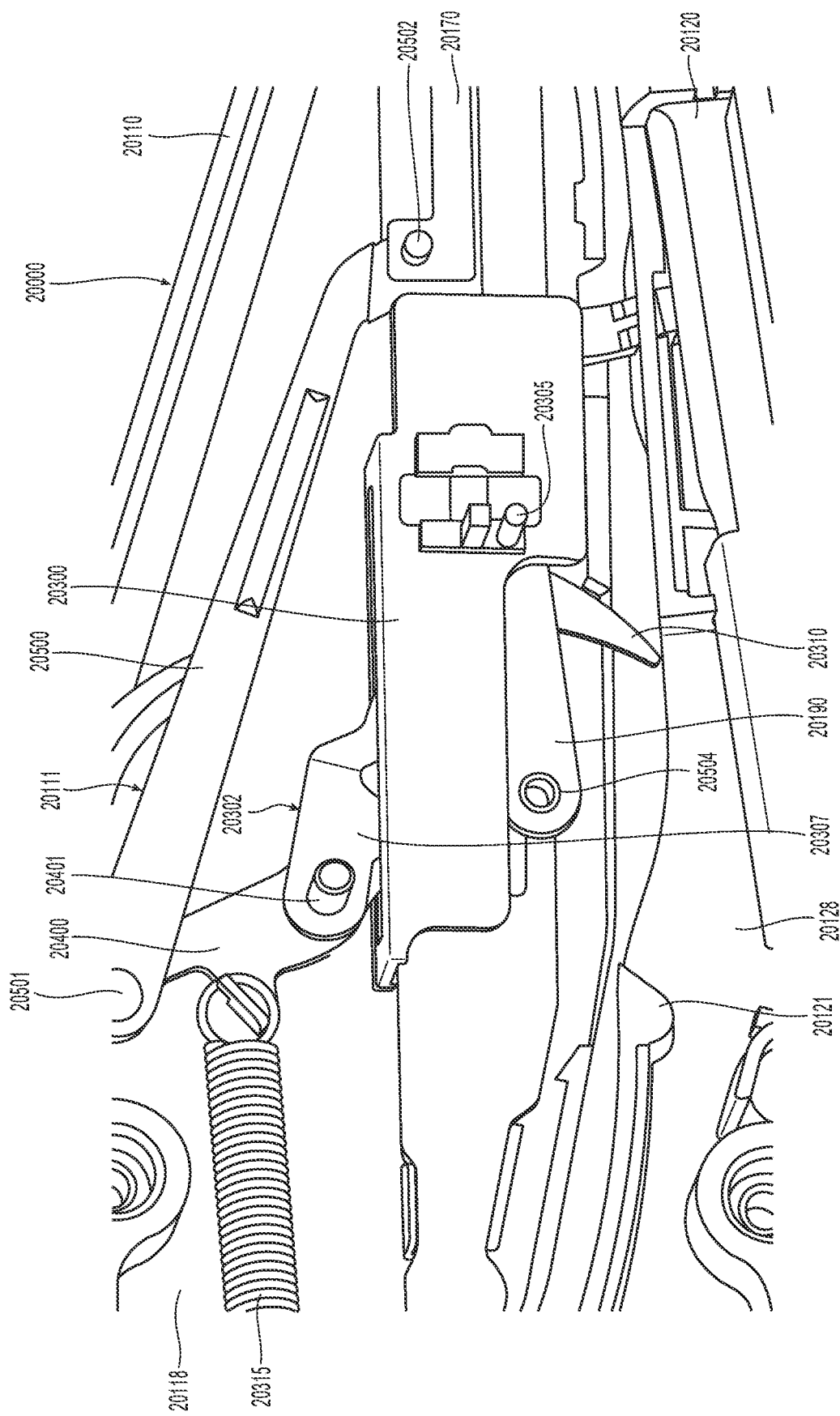
FIGS. 12A-12B are internal, side perspective views of another embodiment of a knife kickout according to the present disclosure.

As best shown in FIG. 12A, knife kickout mechanism 20302 is attached at one end 20307 to link 20400 via pivot 20401 and configured to fit through the trigger carrier 20300 to ultimately have the opposite end 20310 project from a bottom of shaft member 20110. Link 20400 is pivotably coupled at one end to link 20190 via pivot 20504 and an opposite end to link 20500 via pivot 20501. It is important to note that the knife kickout mechanism 20302 is connected to pivot 20401 on one side of link 20400 and is configured to rotate through trigger carrier 20300 on an opposite side of link 20190, the purposes of which will be explained in more detail below.

A midportion 20308 of knife kickout mechanism 20302 is configured to abut a trigger pin 20305 associated with a trigger 20150 during knife actuation and knife return as explained in more detail below. Trigger pin 20305 operably engages trigger 20150 to the trigger carrier 20300 and is configured to reciprocate within a channel 20303 defined in the trigger carrier 20300 upon actuation of the trigger 20150.

As mentioned above, one end 20307 of the knife kickout mechanism 20302 is pivotably coupled to link 20400 which is, in turn, operably coupled to link 20500 via pivot 20501 which is supported within an arcuate channel 20111 defined within shaft 20110. The other end of link 20500 operably connects to the knife carrier 20170 via pin 20502. Pivot 20501 is configured to ride along channel 20111 to facilitate smooth translation of the knife (not shown).

Much like the links discussed above, link 20400 is configured to operably couple to a knife return spring 20315. Knife return spring 20315 is biased in a proximal-most position, which, in turn, biases the trigger 20150 in a distal-most position. Due to the inherent issues associated with sealing and cutting tissue, e.g., tissue sticking to the knife, it is possible that the bias associated with the knife return spring 20315 may not be enough to return the knife and trigger 20150 after actuation. The incorporation of the knife kickout mechanism 20302 provides additional mechanical advantage to return the knife to retracted or at-rest or proximal-most position.

Figure 12B:
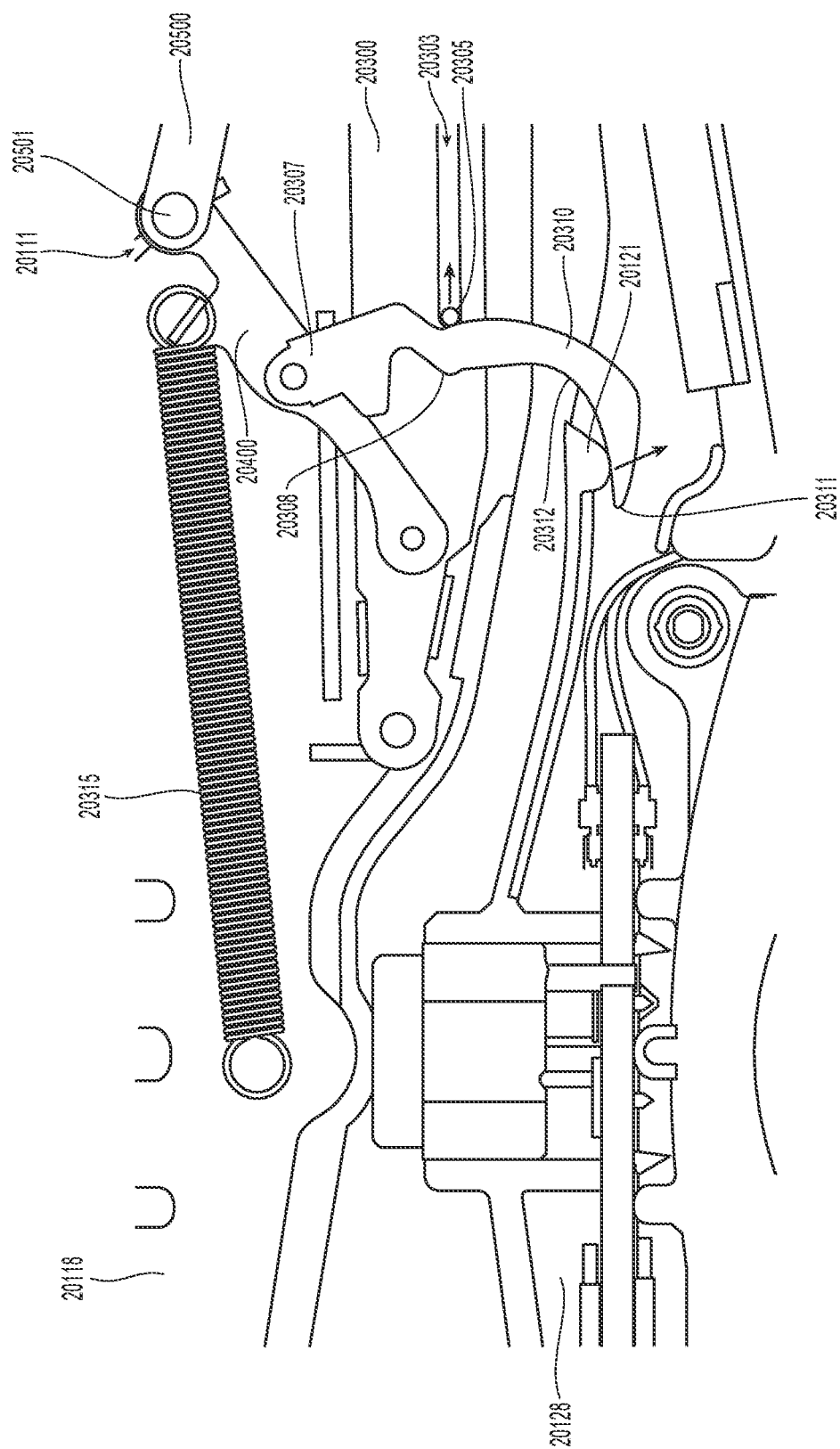

As best shown in FIGS. 14A-14G, when the trigger 20150 is in an unactuated, at react or distal-most position, a distal end 20310 of the knife kickout mechanism 20302 is configured to project towards and in alignment with shaft 20120 of forceps 20000. Upon closing of the handles 20118, 20128, the distal end 20310 of the knife kickout mechanism 20302 is rotated about and translated with link 20400 proximally such that a distal-most end 20311 of the knife kickout mechanism 20302 ultimately engages ramp 20121 defined in shaft 20120 (FIG. 12B). Pin 20305 associated with the trigger 20150 forces knife kickout mechanism 20302 proximally as the trigger 20150 is actuated proximally forcing an upper portion 20312 of the distal end 20310 of knife kickout mechanism 20302 under ramp 20121. Simultaneously, link 20400 forces link 20500 distally along arcuate channel 20111 against the bias of knife spring 20315 to force knife carrier 20170 distally.

In stepped fashion, FIGS. 12 and 14A-14G show the range of motion of the deployment and retraction of the knife. More particularly, FIG. 12A shows an at rest position for trigger 20150 wherein link 20500 is disposed in a proximal-most position within arcuate channel 20111 along with the upper end 20307 of link 20400 in a proximal-most position while pivotably coupled to link 20500. In turn, knife kickout mechanism 20302 is rotated to a distal-most position within shaft 20110.

Figure 14A:
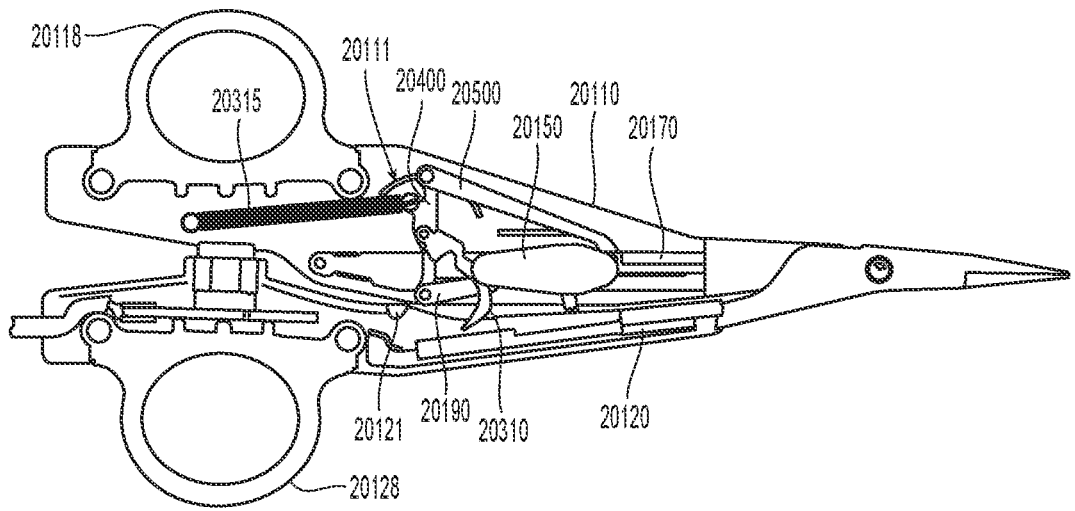
FIGS. 14A-14G are internal, side views showing the range of motion of the knife kickout through the range of actuation of opposing shaft members and the trigger.
Figure 14B:
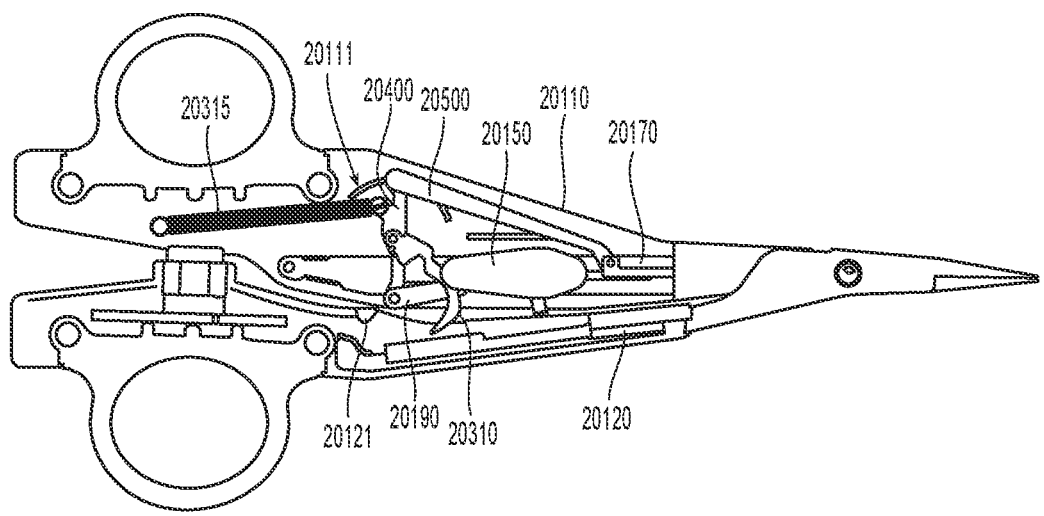
Figure 14C:
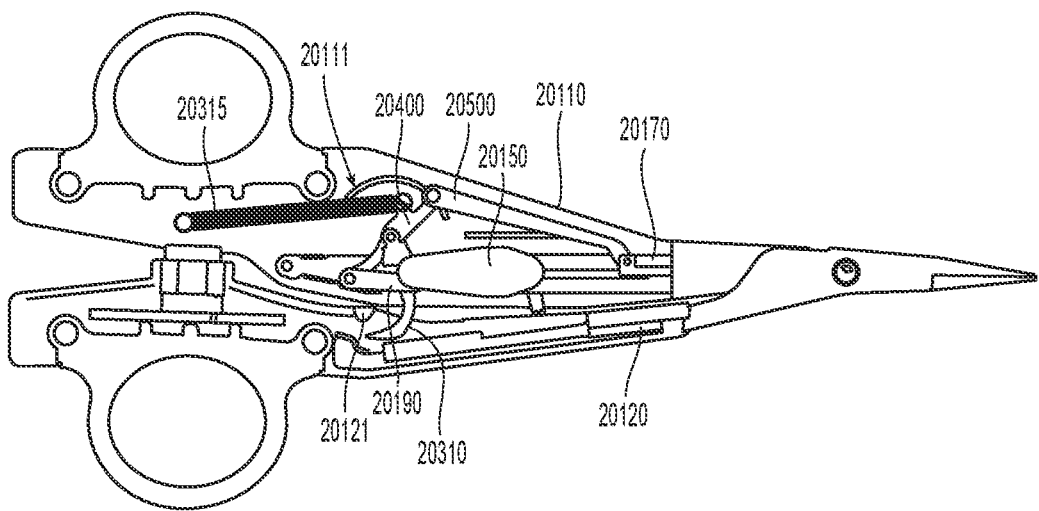
Figure 14D:
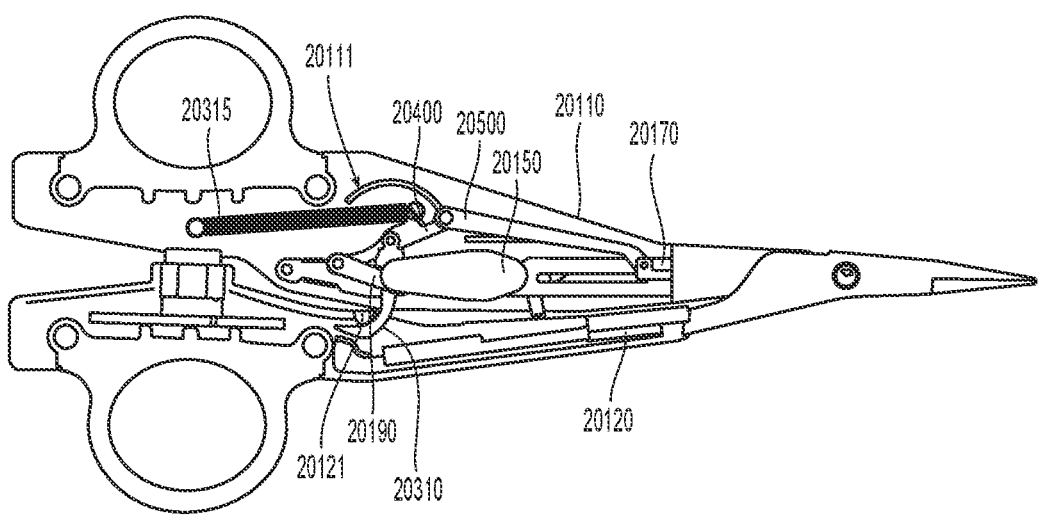

Upon initial movement of trigger 20150 as shown in FIG. 14A, link 20500 is forced by the trigger 20150 distally along arcuate channel 20111 carrying link 20400 along therewith against the bias of spring 20315. As link 20400 moves distally with link 20500, knife kickout mechanism 20302 is initially moved with link 20400 generally toward shaft 20120 prior to moving proximally. As trigger 20150 is moved further proximally, link 20500 continues to traverse arcuate channel 20111 reaching a point wherein link 20400 begins to force the distal end 20310 of the knife kickout mechanism 20302 further towards shaft 20120 and proximally towards ramp 20121 (FIGS. 14B and 14C).

Further actuation of trigger 20150 causes link 20500 to substantially bottom out in arcuate channel 20111 wherein the upper portion 20312 of the distal end 20310 of the knife kick mechanism 20302 engages the ramp 20121 disposed in shaft 20120. During the final stages of movement of the trigger 20150, the trigger pin 20305 assists in moving the distal end 20310 of the knife kickout mechanism 20302 proximally to facilitate engagement with ramp 20121. At this stage the knife return spring 20315 is extended within shaft 20110 to its maximum available bias. Moreover, when the trigger 20150 is fully actuated, the knife (not shown) is fully extended between jaw members 210, 220 (FIG. 1A).

Figure 14E:
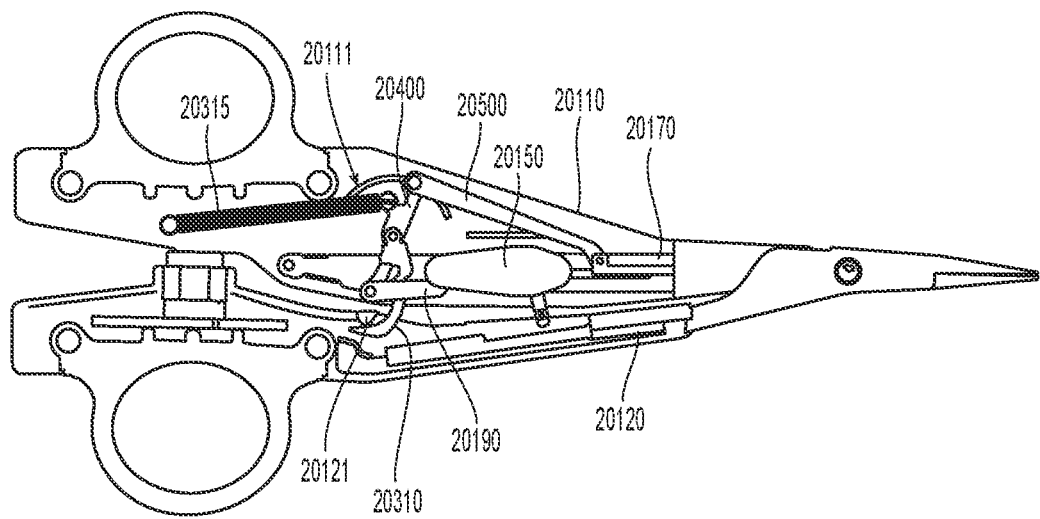
Figure 14F:
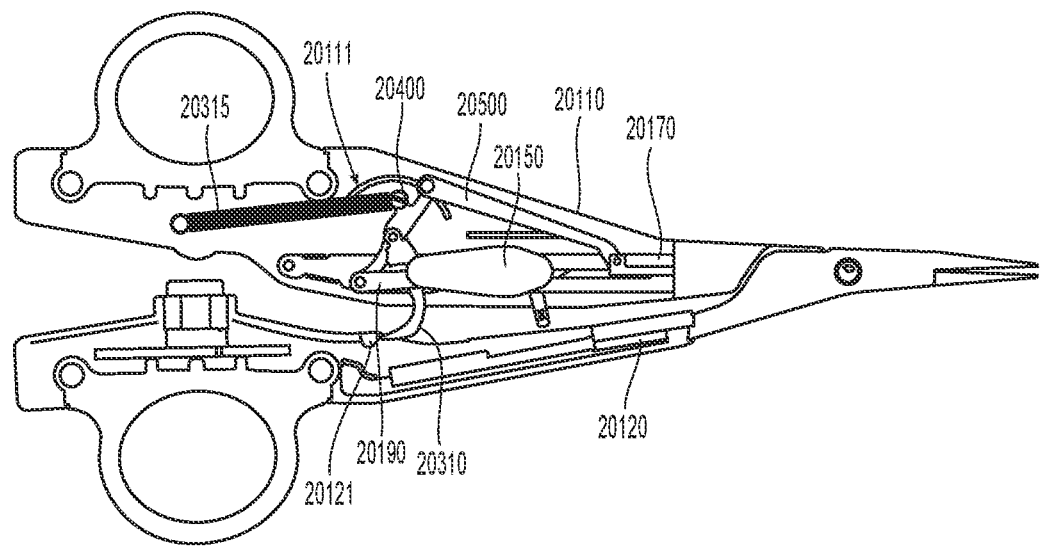
Figure 14G:
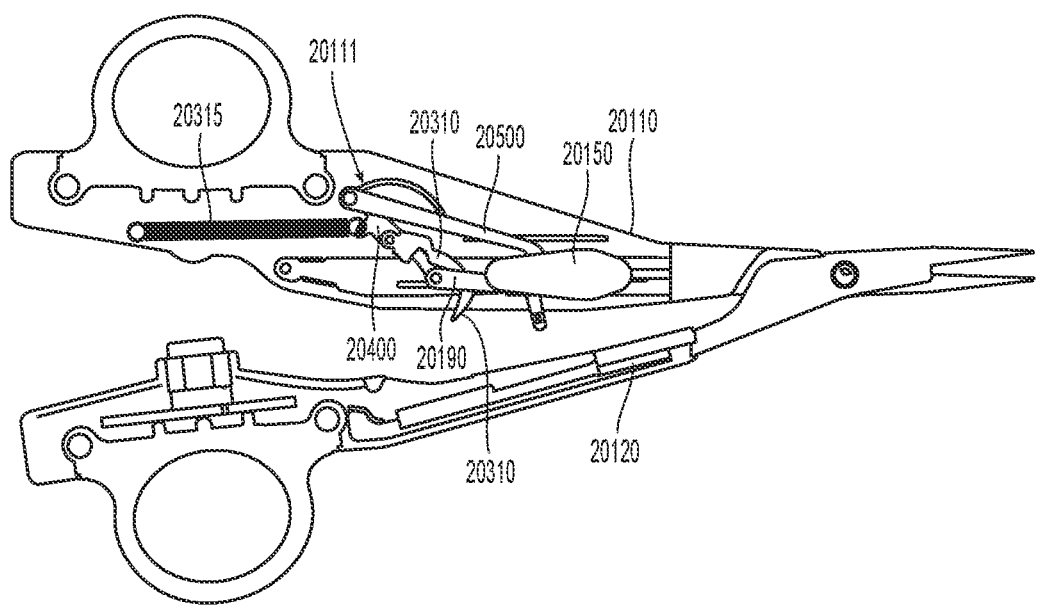

Upon release of the trigger 20150 as shown in FIGS. 14E-14G, the knife return spring 20315 typically has enough bias to return the trigger 20150, the knife, links 20500 and 20400, and knife kickout mechanism 20302 to their respective at rest positions. If the knife sticks on tissue or otherwise gets stuck within the knife channels (not shown), the knife return spring 20315 may not have enough force to return all of the aforementioned components to their respective at rest positions. The knife kickout mechanism 20302 and link 20190 safeguard against this issue.

More particularly, if the knife is caught in the knife channels or otherwise stuck and the various mechanisms (i.e., trigger 20150, the knife, links 20500 and 20400, and knife kickout mechanism 20302) do not return under the normal bias of knife return sprig 20315, the user simply opens the forceps 20000 to facilitate knife recovery. In other words, as the two shaft members 20110, 20120 are moved away from one another, the curvature of the upper portion 20312 of the distal end 20310 of the knife kickout mechanism 20302 against the ramp 20121 forces or kicks the knife kickout mechanism 20302 distally which, in turn, forces link 20400 and link 20500 proximally. As the links 20400 and 20500 are forced proximally, the bias of the knife return spring 20315 may at some point be enough to return the various components to their respective at rest positions as best shown in FIGS. 14F and 14G.

As an additional safeguard, the knife kickout mechanism 20302 also operably engages the trigger pin 20305 proximal a mid-section 20308 thereof. In other words, during the initial knife kickout, a middle portion 20308 of the knife kickout mechanism 20302 forces the trigger pin 20305 distally in the range of motion. As can be appreciated, this provides further assistance to the knife return (FIG. 12B).

As a last resort to prevent the knife from sticking and as mentioned above, the unique arrangement of the knife kickout mechanism 20302 through the trigger carrier 20300, i.e., disposed between or on opposite sides of links 20400 and 20190, forces the knife kickout mechanism 20302 distally to the at rest position which, in turn, forces the other components, i.e., link 20400, link 20500, trigger 20150 and knife, to their respective at rest positions. More particularly, at the final stages of return, link 20190 abuts the knife kickout mechanism 20302 to force the knife kickout mechanism 20302 distally assuring full trigger 20150 and knife return.

Figure 13A:
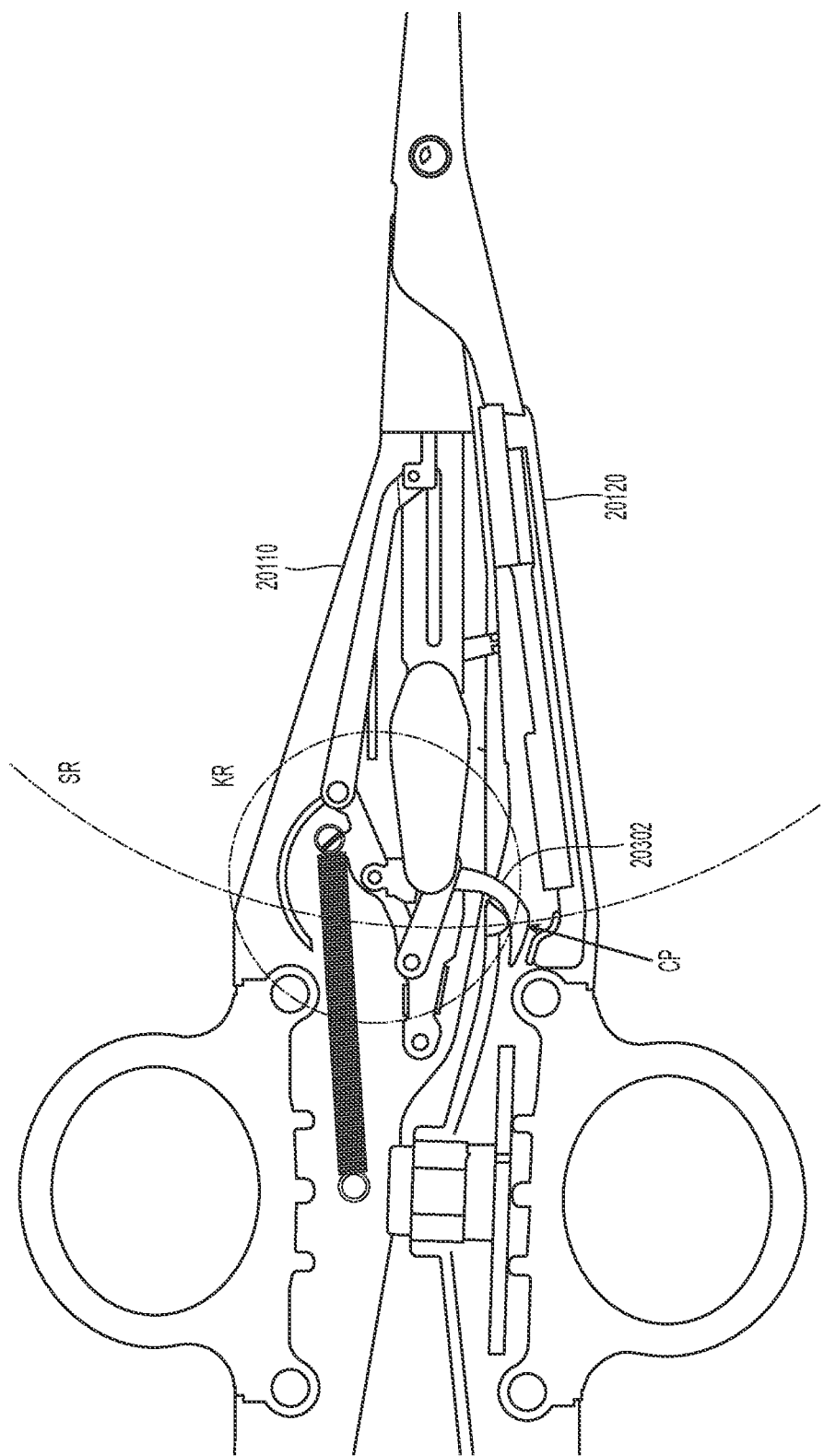
FIGS. 13A-13B are internal, side views showing the rotational path of the knife kickout according to the present disclosure.
Figure 13B:
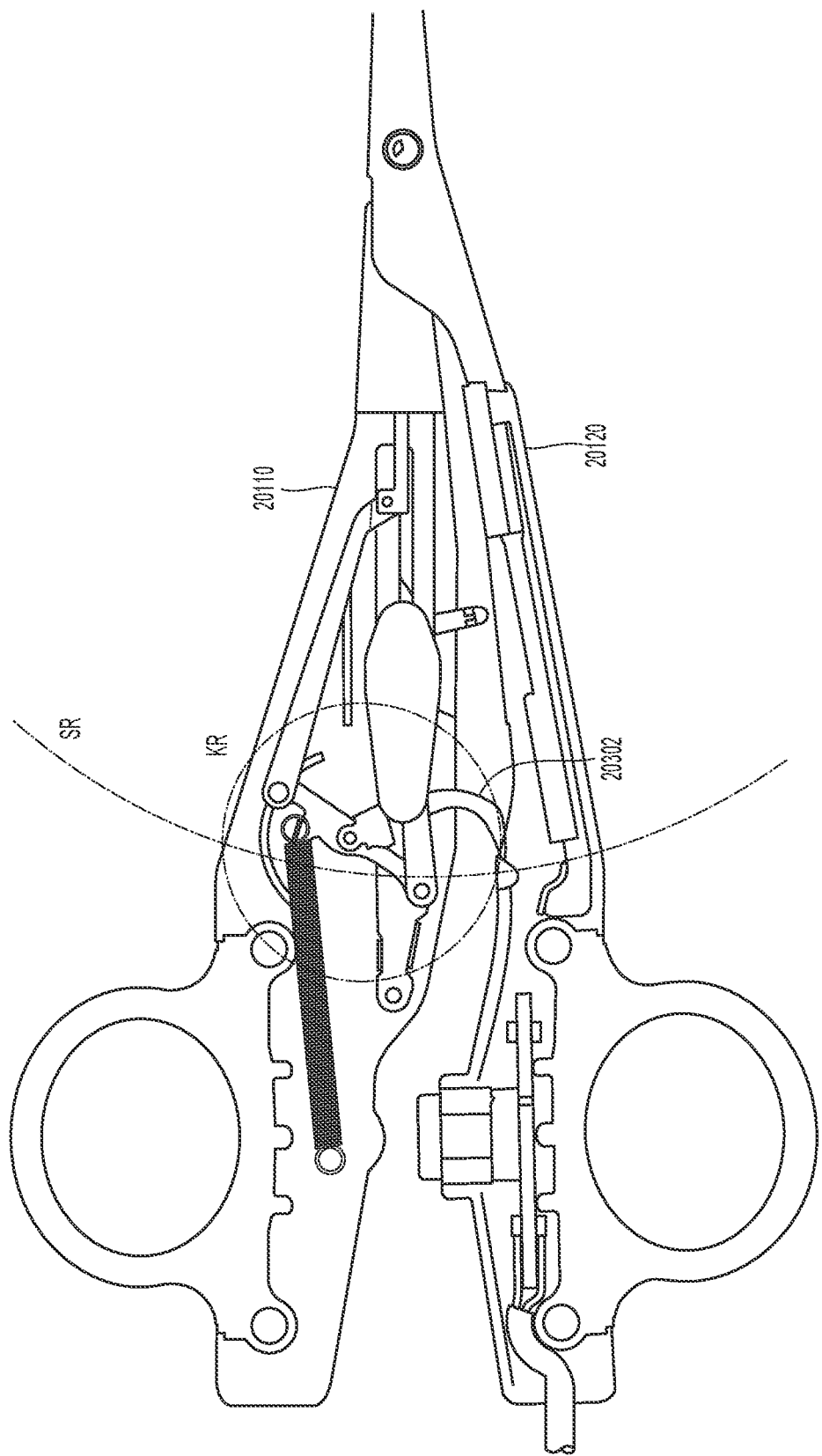

FIGS. 13A and 13B show the arcuate path of rotation (SR) for the shafts 20110, 20110 compared to the arcuate path of rotation (KR) of the knife kickout mechanism 20302. Constructing the knife kickout mechanism 20302 with an independent rotation path allows for more kickout design freedom without being dependent on the shaft rotation (SR) or the motion of the other components associated therewith. The separate arcuate pivot rotation (KR) of the knife kickout mechanism 20302 also allows the kickout contact point CP to move along the kickout surface further facilitating knife return.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
   first and second shaft members each having a jaw member disposed at a distal end thereof, the first and second shaft members configured to rotate about a first pivot to move the jaw members between an open position and a closed position, the first and second shaft members defining a longitudinal axis therebetween;
   a knife deployment mechanism disposed within the first shaft member and including a trigger moveable along the longitudinal axis to deploy a knife operably coupled thereto between a retracted position relative to the jaw members and an extended position between the jaw members, the knife deployment mechanism including at least a first link, a second link and a third link that cooperate with a knife carrier to actuate the knife from the retracted position to the extended position between the jaw members upon actuation of the trigger; and
   a knife kickout mechanism pivotably coupled to the second link and configured to engage a ramp disposed in the second shaft member upon approximation of the first and second shaft members, the knife kickout mechanism configured to cooperate with the first, second and third links to urge the knife back to the retracted position upon opening of the first and second shaft members.

2. The electrosurgical forceps according to claim 1, wherein the third link is configured to operably engage the knife kickout mechanism to facilitate return of the knife kickout mechanism to an at rest position.

3. The electrosurgical forceps according to claim 1, wherein at least one of the first and second links is operably coupled to a spring to bias the knife in an at rest position.

4. The electrosurgical forceps according to claim 1, wherein the first link is configured to travel in an arcuate channel defined within the first shaft member to facilitate smooth translation of the knife.

5. The electrosurgical forceps according to claim 1, wherein the knife kickout mechanism is configured to rotate about a second pivot operably coupled to the second link.

6. The electrosurgical forceps according to claim 5, wherein the path of rotation of the knife kickout mechanism about the second pivot is different than the path of the rotation of the first and second shaft members about the first pivot.

7. The electrosurgical forceps according to claim 1, wherein the knife kickout mechanism includes an upper portion having a curved surface to facilitate engagement and disengagement with the ramp.

8. The electrosurgical forceps according to claim 7, wherein the knife kickout mechanism is disposed on opposite sides of the second link and the third link.

9. The electrosurgical forceps according to claim 8, wherein the third link is configured to operably engage the knife kickout mechanism if the knife is inhibited from returning to the retracted position, a range of motion of the third link, upon returning to an at rest position, configured to operably engage the knife kickout mechanism and facilitate return of the knife kickout mechanism and the trigger to an at rest position.

\* \* \* \* \*